United States Patent [19]

Kelly

[11] 4,124,599
[45] Nov. 7, 1978

[54] ENLARGED-HETERO-RING PROSTACYCLIN ANALOGS

[75] Inventor: Robert C. Kelly, Kalamazoo, Mich.

[73] Assignee: The Upjohn Company, Kalamazoo, Mich.

[21] Appl. No.: 819,941

[22] Filed: Jul. 28, 1977

Related U.S. Application Data

[63] Continuation-in-part of Ser. No. 725,547, Sep. 22, 1976, abandoned, which is a continuation-in-part of Ser. No. 716,771, Aug. 23, 1976, abandoned.

[51] Int. Cl.$^2$ .................... C07D 311/02; A61K 31/35
[52] U.S. Cl. ................................. 260/345.2; 542/426; 542/439; 542/441; 542/447; 424/283
[58] Field of Search ...................... 542/426; 260/345.2

[56] References Cited

PUBLICATIONS

Pace-Asciak et al., Biochem., 10, 3657 (1971).
Pace-Asciak et al., Jacs., 98, 2348 (1976).

*Primary Examiner*—Nicky Chan
*Attorney, Agent, or Firm*—Morris L. Nielsen

[57] ABSTRACT

Prostaglandin (PG$_1$) derivatives having (1) a 6-keto feature, together with a 9-deoxy-9-hydroxymethyl feature for example

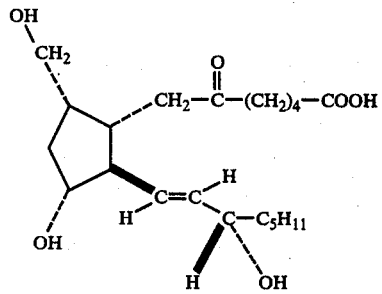

or (2) a 9-deoxy-6,9-epoxymethano feature together with a 5-halo or 6-hydroxy feature, for example

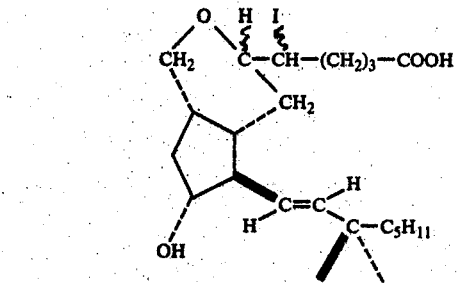

or

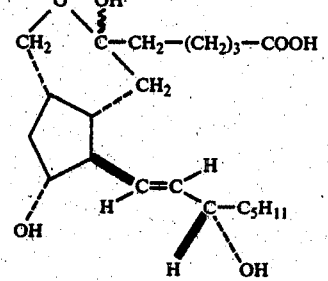

or a 5,6-didehydro feature, for example in an enol ether of the formula

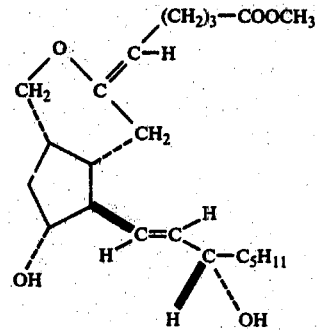

said derivatives having pharmacological activity. Processess for preparing them and the appropriate intermediates are disclosed.

23 Claims, No Drawings

ENLARGED-HETERO-RING PROSTACYCLIN ANALOGS

CROSS REFERENCE TO RELATED APPLICATIONS

This application is a continuation-in-part of copending application Ser. No. 725,547 filed Sept. 22, 1976, now abandoned, which was a continuation-in-part of then copending application Ser. No. 716,771 filed Aug. 23, 1976, since abandoned.

BACKGROUND OF THE INVENTION

This invention relates to prostaglandin derivatives and to a process for preparing them.

The prostaglandins and analogs are well-known organic compounds derived from prostanoic acid which has the following structure and atom numbering:

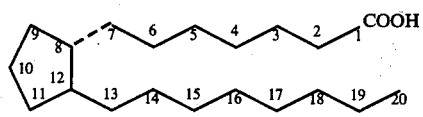

As drawn hereinafter the formulas represent a particular optically active isomer having the same absolute configuration as $PGE_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background on prostaglandins, see for example Bergstrom et al., Pharmacol. Rev. 20, 1 (1968). For related compounds see Pace-Asciak et al., Biochem. 10, 3657 (1971). Related compounds are described in a publication on 6-keto-prostaglandin $F_{1\alpha}$ by Pace-Asciak, J. Am. Chem. Soc. 98, 2348 (1976) and a publication on "PGX" (6,9α-oxido-9α,15α-dihydroxyprosta-(Z)5, (E)13-dienoic acid) by E. J. Corey et al., J. Am. Chem. Soc. 99, 20006 (1977).

Some of the compounds of this invention may be regarded as analogs of prostacyclin and prostacyclin-type compounds.

Prostacyclin, an organic compound related to prostaglandins, is (5Z)-9-deoxy-6,9α-epoxy-$\Delta^5$-$PGF_1$ and is represented by the formula

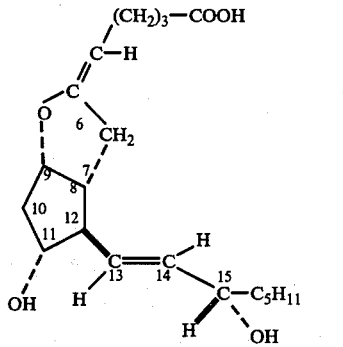

For its synthesis and structure see for example R. A. Johnson et al., J. Am. Chem. Soc. 99, 4182 (1977) and Prostaglandins 12, 915 (1976), and E. J. Corey et al., cited above. For some of its biological properties and uses see the references cited in the Johnson references.

Prostacyclin is referred to as "$PGI_2$", see Anonymous, Prostaglandins 13, 375 (1977).

Prostacyclin and prostacyclin-type compounds, including derivatives and analogs, are extremely potent in causing various biological responses. For that reason, these compounds are useful for pharmacological purposes. A few of those biological responses are: inhibition of blood platelet aggregation, stimulation of smooth muscle, inhibition of gastric secretion and reduction of undesirable gastrointestinal effects from systemic administration of prostaglandin synthetase inhibitors.

Because of these biological responses, prostacyclin and prostacyclin-type compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

Prostacyclin and prostacyclin-type compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent postoperative surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intrevenous route of administration is preferred. Doses in the range about 0.01 to about 10 mg. per kg. of body weight per day are used, the exact dose depending on the age, weight, and condition of the patient or animal, and on the frequency and route of administration.

The addition of prostacyclin and prostacyclin-type compounds to whole blood provides in vitro applications such as storage of whole blood to be used in heart-lung machines. Additionally whole blood containing these compounds can be circulated through limbs and organs, e.g. heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the recipient, or to two or all of those at a total steady state dose of about 0.001–1.0 μg./ml. of whole blood. These compounds are also useful in preparing platelet-rich concentrates from blood for use in treating thrombocytopenia or in chemotherapy.

Prostacyclin and prostacyclin-type compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the later purpose, the compound is administered by intravenous infusion immediately after abortion or delivery at a dose in the range about 0.01 to about 50 µg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

Prostacyclin and prostacyclin-type compounds are also useful in mammals, including man and certain useful animals, e.g. dogs and pigs, to reduce and control excessive gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg. per kg. of body weight per minute, or in a total daily dose by injection of infusion in the range about 0.01 to about 10 mg. per kg. of body weight per day, the exact dose depending on the age, weight, and condition of the patient or animal, and on the frequency and route of administration.

Prostacyclin and prostacyclin-type compounds are also useful in reducing the undesirable gastrointestinal effects resulting from systemic administration of anti-inflammatory prostaglandin synthetase inhibitors, and are used for that purpose by concomitant administration of the prostacyclin or prostacyclin-type compound and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins of the E and A series, including $PGE_1$, $PGE_2$, $PGE_3$, 13,14-dihydro-$PGE_1$, and the corresponding 11-deoxy-PGE and PGA compounds. Prostacyclin and prostacyclin-type compounds are useful, for example, in reducing the undesirable gastrointestinal effects resulting from systemic administration of indomethacin, phenylbutazone, and aspirin. These are substances specifically mentioned in Partridge et al., as non-steroidal, anti-inflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

The prostacyclin or prostacyclin-type compound is administered along with the anti-inflammatory prostaglandin synthetase inhibitor either by the same route of administration or by a different route. For example, if the anti-inflammatory substance is being administered orally, the prostacyclin or prostacyclin-type compound is also administered orally, or, alternatively, is administered rectally in the form of a suppository or, in the case of women, vaginally in the form of a suppository or a vaginal device for slow release, for example as described in U.S. Pat. No. 3,545,439. Alternatively, if the anti-inflammatory substance is being administered rectally, the prostacyclin or prostacyclin-type compound is also administered rectally. Further, the prostacyclin derivative can be conveniently administered orally or, in the case of women, vaginally. It is especially convenient when the administration route is to be in the same for both anti-inflammatory substance and prostacyclin or prostacyclin-type compound to combine both into a single dosage form.

The dosage regimen for the prostacyclin or prostacyclintype compound in accord with this treatment will depend upon a variety of factors, including the type, age, weight, sex and medical condition of the mammal, the nature and dosage regimen of the anti-inflammatory synthetase inhibitor being administered to the mammal, the sensitivity of the particular prostacyclin or prostacyclin-type compound to be administered. For example, not every human in need of an anti-inflammatory substance experiences the same adverse gastrointestinal effects when taking the substance. The gastrointestinal effects will frequently vary substantially in kind and degree. But it is within the skill of the attending physican or veterinarian to determine that administration of the anti-inflammatory substance is causing undesirable gastrointestinal effects in the human or animal subject and to prescribe an effective amount of the prostacyclin or prostacyclin-type compound to reduce and then substantially to eliminate those undesirable effects.

Prostacyclin or prostacyclin-type compounds are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use the prostacyclin or prostacyclin-type compound can be combined advantageously with other anti-asthmatic agents, such as sympathominetics (isoproterenol, phenylephrine, ephedrine, etc.); xanthine derivatives (theophylline and aminophylline); and corticosteroids (ACTH and prednisolone).

Prostacyclin or prostacyclin-type compounds are effectively administered to human asthma patients by oral inhalation or by aerosol inhalation.

For administration by the oral inhalation route with conventional nebulizers or by oxygen aerosolization it is convenient to provide the prostacyclin ingredient in dilute solution, preferably at concentrations of about 1 part of medicament to form about 100 to 200 parts by weight of total solution. Entirely conventional additives may be employed to stabilize these solutions or to provide isotonic media, for example, sodium chloride, sodium citrate, citric acid, and the like can be employed.

For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

Prostacyclin or prostacyclin-type compounds are useful in mammals, including man, as nasal decongestants and are used for this purpose in a dose range of about 10 $\mu$g. to about 10 mg. per ml. of a pharmacologically suitable liquid vehicle or as an aerosol spray, both for topical application.

Prostacyclin or prostacyclin-type compounds are also useful in treating peripheral vascular disease in humans. The term peripheral vascular disease as used herein means disease of any of the blood vessels outside of the heart and to disease of the lymph vessels, for example, frostbite, ischemic cerebrovascular disease, arteriovenous fistulas, ischemic leg ulcers, phlebitis, venous insufficiency, gangrene, hepatorenal syndrome, ductus arteriosus, nonobstructive mesenteric ischemia, arteritis lymphangitis and the like. These examples are included to be illustrative and should not be construed as limiting the term peripheral vascular disease. For these conditions the prostacyclin compounds are administered orally or parenterally via injection or infusion directly into a vein or artery.

The dosages of such compounds are in the range of 0.01–1.0 $\mu$g. administered by infusions at an hourly rate or by injection on a daily basis, i.e. 1–4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed.

Prostacyclin or prostacyclin-type compounds are accordingly useful for treating peripheral vascular diseases in the extremities of humans who have circulatory insufficiencies in said extremities, such treatment affording relief of rest pain and induction of healing of ulcers.

For a complete discussion of the nature of and clinical manifestations of human peripheral vascular disease and the method previously known of its treatment with prostaglandins see South African Pat. No. 74/0149 referenced as Derwent Farmdoc No. 58,400V. See Elliott, et al., Lancet Jan. 18, 1975, pp. 140–142. Prostacyclin or prostacyclin-type compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor. i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

Prostacyclin or prostacyclin-type compounds are further useful for controlling the reproductive cycle in menstruating female mammals, including humans. By the term menstruating female mammals is meant animals which are mature enough to menstruate, but not so old that regular menstruation has ceased. For that purpose the prostacyclin compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

Prostacyclin or prostacyclin-type compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by prostacyclin compounds is also useful in operative gynecology such as D and C (Cervical Dilation and Uterine Curettage) where mechanical dilation may cause performation of the uterus, cervical tears, or infections. It is also useful for diagnostic procedures where dilation is necessary for tissue examination. For these purposes, the prostacyclin compound is administered locally or systemically.

The prostacyclin compound, for example, is administered orally or vaginally at doses of about 5 to 50 mg. per treatment of an adult female human, with from one to five treatments per 24 hour period. Alternatively the compound is administered intramuscularly or subcutaneously at doses of about one to 25 mg. per treatment. The exact dosages for these purposes depend on the age, weight, and condition of the patient or animal.

Prostacyclin and prostacyclin-type compounds are further useful in domestic animals as in abortifacients (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The prostacyclin compound is injected or applied in a feed at doses of 0.1–100 mg. per animal and may be combined with other agents such as steroids. Dosing schedules will depend on the species treated. For example, mares are given the prostacyclin compound 5 to 8 days after ovulation and return to estrus. Cattle are treated at regular intervals over a 3 week period to advantageously bring all into estrus at the same time.

Prostacyclin or prostacyclin-type compounds increase the flow of blood in the mammalian kidney, thereby increasing volume and electrolyte content of the urine. For that reason, these compounds are useful in managing cases of renal dysfunction, especially those involving blockage of of renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 μg. per kg. of body weight or per kg. of body weight per minute until the desired effect is obtained. Subsequent doses are given by intravenous, intramuscular, or subcutaneous injection or infusion in the range 0.05 to 2 mg. kg. of body weight per day.

Prostacyclin or prostacyclin-type compounds are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, nonmalignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness or noticeably but incompletely cleared or completely cleared.

For those purposes, such compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or perilesionally, or subcutaneously, using appropriate sterile saline compositions.

Prostacyclin or prostacyclin-type compounds are useful as antiflammatory agents for inhibiting chronic inflammation in mammals including the swelling and other unpleasant effects thereof using methods of treatment and dosages generally in accord with U.S. Pat. No. 3,885,041, which patent is incorporated herein by reference.

Other compounds of this invention, having the 6-keto feature, are analogs of prostaglandins. Prostaglandins, as known in the art, have pharmacological activity and are accordingly useful for many purposes similar to those described above for prostacyclin and prostacyclin-type compounds and are administered in similar fashion.

SUMMARY OF THE INVENTION

It is the purpose of this invention to provide novel products having pharmacological activity. It is a further purpose to provide processes for preparing these products and their intermediates.

Accordingly, there is provided a compound of the formula:

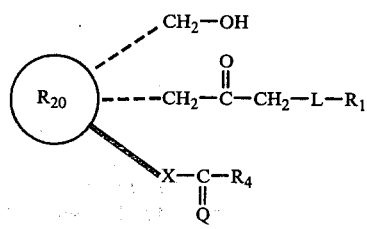

or a mixture comprising that compound and the enantiomer thereof
wherein $R_{20}$ is

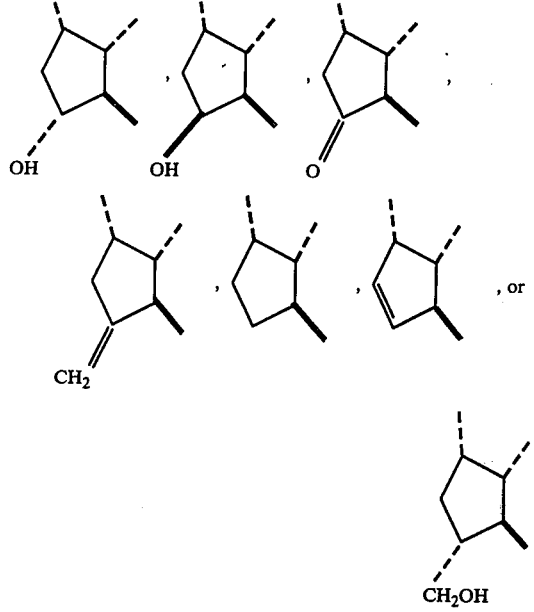

wherein L is
(1) —(CH$_2$)$_d$—C(R$_2$)$_2$—
(2) —CH$_2$—O—CH$_2$—Y— or
(3) —CH$_2$CH=CH— wherein $d$ is zero to 5, $R_2$ is hydrogen, methyl, or fluoro, being the same or different with the proviso that one $R_2$ is not methyl when the other is fluoro, and Y is a valence bond, —CH$_2$— or —(CH$_2$)$_2$—,
wherein Q is

wherein $R_8$ is hydrogen or alkyl of one to 4 carbon atoms, inclusive,
wherein $R_1$ is
(1) —COOR$_3$
(2) —CH$_2$OH
(3) —CH$_2$N(R$_9$)(R$_{18}$)

(4)

(5)

wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

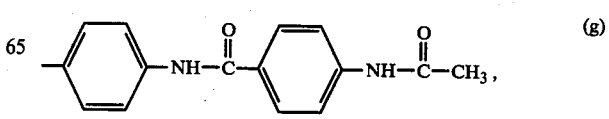

(g)

-continued (h) 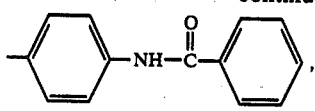, (i) 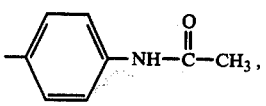, (j) 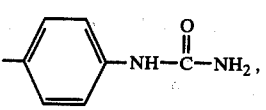, (k) 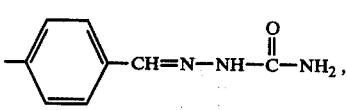, (l) 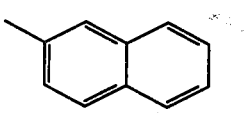

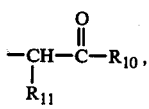

(m) $-\overset{}{\underset{R_{11}}{CH}}-\overset{O}{\overset{\|}{C}}-R_{10}$, wherein $R_{10}$ is phenyl, p-bromophenyl, p-biphenylyl, p-nitrophenyl, p-benzamidophenyl, or 2-naphthyl, and wherein $R_{11}$ is hydrogen or benzoyl, or (n) a pharmacologically acceptable cation, wherein $R_9$ is hydrogen, methyl, or ethyl, and $R_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;
wherein $R_4$ is (1) 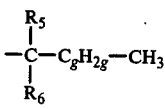

(2) 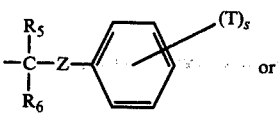 or (3) 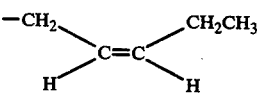

wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro and the further proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, with one to 6 carbon atoms, inclusive between $CR_5R_6$— and the phenyl ring; wherein T is alkyl of one to 4 carbon atoms, inclusive, fluoro, chloro, trifluoromethyl, or —$OR_7$— wherein $R_7$ is alkyl of one to 4 carbon atoms, inclusive, and s is zero, one, 2 or 3, with the proviso that not more than two T's are other than alkyl and when s is 2 or 3 the T's are either the same or different; and
wherein X is
(1) trans—CH=CH—
(2) cis—CH=CH—
(3) —C≡C— or
(4) —CH$_2$CH$_2$—;
including the lower alkanoates thereof.

There are likewise provided compounds of the formula

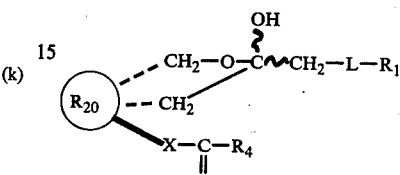 II

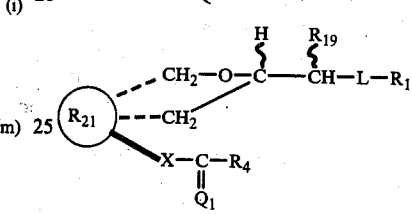 III and

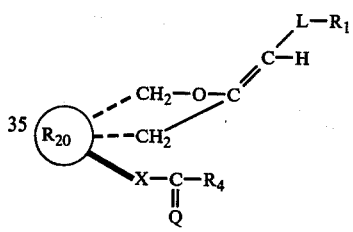 IV wherein $R_{20}$, L, Q, $R_1$, $R_4$, and X are as defined above for formula I.

In compounds of formula III, $R_{19}$ is chloro, bromo, or iodo. In compounds of formula II and III, the wavy line ~ indicates attachment in alpha or beta configuration.
In compounds of formula III, $Q_1$ is

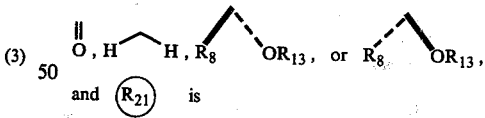

and $R_{21}$ is

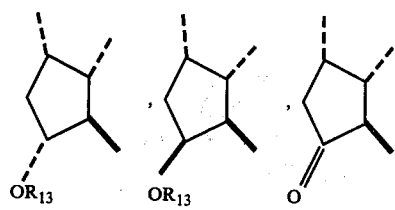

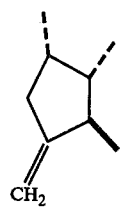

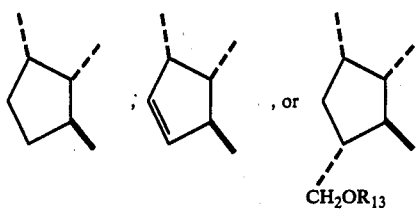

CH₂OR₁₃

In formula III, R₁₃ is (a) hydrogen, (b) tetrahydropyranyl, (c) tetrahydrofuranyl, (d) 1-ethoxyethyl, (e) a group of the formula

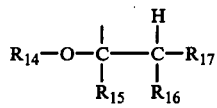

wherein R₁₄ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein R₁₅ and R₁₆ are the same or different, being hydrogen, alkyl of one to 4 carbon atoms, inclusive, phenyl or phenyl substituted with one, 2, or 3 alkyl of one to 4 carbon atoms, inclusive, or, when R₁₅ and R₁₆ are taken together —(CH₂)a— or —(CH₂)b—O—(CH₂)c— wherein a is 3, 4, or 5, b is one, 2, or 3, and c is one, 2, or 3 with the proviso that b plus c is 2, 3, or 4, and wherein R₁₇ is hydrogen or phenyl, or (f) carboxyacyl including

  (a')

wherein "A" is alkyl of one to 4 carbon atoms, inclusive, bromo, phenylalkyl of 7 to 10 carbon atoms, inclusive, or nitro, and "e" is zero to 5, inclusive, provided that not more than two A's are other then alkyl, and that the total number of carbon atoms in the A's does not exceed 10 carbon atoms,

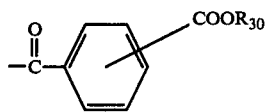  (b')

wherein R₃₀ is alkyl of one to 4 carbon atoms, inclusive,

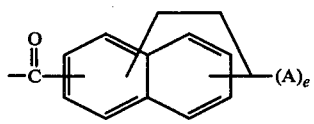  (c')

wherein "A" and "e" is as defined above, or

  (d')

wherein R₃₁ is alkyl of one to 7 carbon atoms, inclusive.

In formulas I–IV as used herein, attachment to R₂₀ and R₂₁ corresponds to bonds to the cyclopentane ring at the C-8, C-9, and C-12 positions following prostaglandin nomenclature, thus:

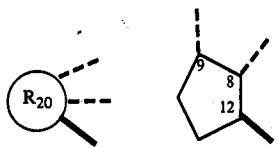

Within the scope of the prostaglandin derivatives described herein there are represented (a) PGF_α compounds when R₂₀ is

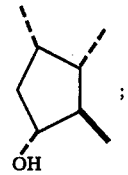

;

(b) 11β-PGF_α compounds when R₂₀ is

;

(c) 11-Deoxy-11-keto-PGF_α compounds when R₂₀ is

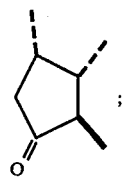

;

(d) 11-Deoxy-11-methylene-PGF_α compounds when R₂₀ is

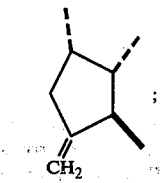

;

(e) 11-Deoxy-PGF_α compounds when R₂₀ is

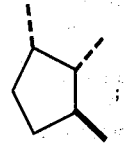

;

(f) 11-Deoxy-10,11-Didehydro-PGF_α compounds when R₂₀ is

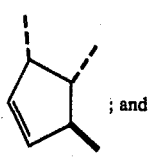

(g) 11-Deoxy-11-hydroxymethyl-PGF$_\alpha$ compounds when ⓡ$_{20}$ is

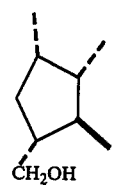

For those compounds of formula I–IV wherein Q is

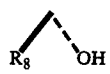

i.e. wherein the C-15 hydroxyl group is attached to the side chain in alpha configuration, the configuration at C-15 is identical with that of the naturally occuring prostaglandins such as PGE$_1$ obtained from mammalian tissues. The 15-epimer compounds are represented by formulas I–IV when Q is

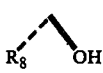

and are identified variously as "15-epi" or "15β" or "15R" by the appropriate prefix in the name. As is known in the art, "R" and "S" designations depend on the neighboring substituents. See. R. S. Cahn, J. Chem. Ed. 41, 116 (1964).

A typical example of the keto compounds of formula I is represented by the formula

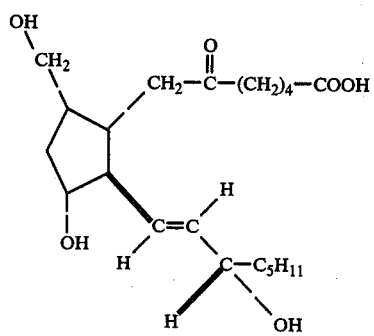

V named 6-keto-9-deoxy-9α-hydroxymethyl-PGF$_1$. The compound of formula V is a species of the formula-1 compounds wherein ⓡ$_{20}$ is

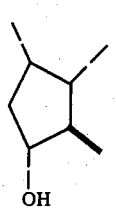

L is —(CH$_2$)$_3$—, Q is

R$_1$ is —COOH, R$_4$ is n-pentyl, and X is trans—CH=CH—.

An example of the hemi-ketal compounds of formula II is represented by the formula

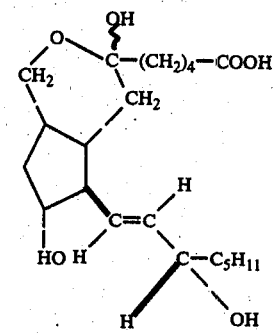

VI named 9-deoxy-6ξ,9α-epoxymethano-6ξ-hydroxy-PGF$_1$.

An example of the halo compounds of formula III is represented by the formula

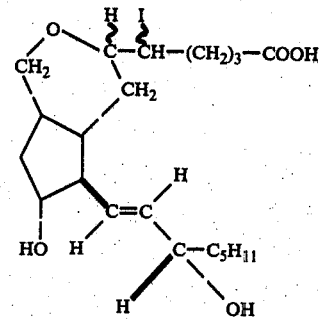

VII and named 5ξ-iodo-9-deoxy-6ξ,9α-epoxymethano-PGF$_1$.

An example of the enol ethers of formula IV is represented by the formula

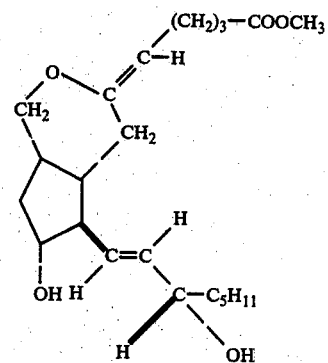

VIII named (5Z)-9-deoxy-6,9α-epoxymethano-Δ$^5$-PGF$_1$, methyl ester.

As to the "Z" and "E" nomenclature for stereoisomerism about a double bond, see for example J. E. Blackwood et al., J. Am. Chem. Soc. 90, 509 (1968).

The formula-I compounds are named as 6-keto-PGF$_{1\alpha}$compounds following prostaglandin nomenclature, with appropriate use of "homo" or "nor" for variations in chain length as known in the art. Likewise, the formula-II compounds are identified as 6-hydroxy compounds and the formula-III compounds are 5-halo compounds, regardless of chain length.

The compounds of formulas II and IV, and those of formula III wherein R$_{13}$ is hydrogen, like prostacyclin and prostacyclin-type compounds, and those of formula I, like prostaglandins, are extremely potent in causing various biological responses. For that reason, these compounds are useful for pharmacological purposes. A few of those biological responses are: inhibition of blood platelet aggregation, stimulation of smooth muscle, inhibition of gastric secretion and reduction of undesirable gastrointestinal effects from systemic administration of prostaglandin synthetase inhibitors.

Because of these biological responses, these novel compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits, and monkeys.

Many of the biological responses known for these 6-keto, iodo-ether, enol-ether, and hemi-ketal prostaglandin derivatives are also known for the older prostaglandin compounds and for the prostacyclin and prostacyclintype compounds. However, these derivatives are surprisingly more specific with regard to potency in causing prostaglandin-like biological responses. Each of these novel derivatives is therefore useful in place of the known prostaglandintype compounds for at least one of the above pharmacological purposes and, moreover, it surprisingly and unexpectedly more useful for that purpose because it causes smaller and fewer undesired side effects than the known prostaglandins.

The compounds of formula III wherein R$_{13}$ is not hydrogen but a blocking group such as tetrahydropyranyl are useful as intermediates in the various processes for preparing other useful compounds as described herein or known in the art. Corresponding derivatives of compounds I, II, and IV with blocking groups are also useful as intermediates.

To obtain the optimum combination of biological response specificity, potency, and duration of activity, certain compounds within the scope of formulas I-IV are preferred. For example it is preferred that Q be

wherein it is especially preferred that R$_8$ be hydrogen, methyl, or ethyl.

When Q is

it is preferred that R$_8$ be methyl or ethyl.

Another preference for the compounds of formulas I-III, as to R$_1$, is that R$_3$ in —COOR$_3$ be either hydrogen or alkyl of one to 12 carbon atoms, inclusive, or a salt of a pharmacologically acceptable cation. Further, when R$_3$ is alkyl, it is more preferred that it be alkyl of one to 4 carbon atoms, and especially methyl or ethyl.

For the compounds of formula IV, as to R$_1$, it is preferred that R$_3$ in —COOR$_3$ be alkyl of one to 12 carbon atoms, inclusive, or a salt of a pharmacologically acceptable cation. When R$_3$ is alkyl, it is more preferred that it be alkyl of one to 4 carbon atoms, especially methyl or ethyl.

For purposes of stability on long storage it is preferred for the compounds of formula I-IV that R$_3$ in —COOR$_3$ be amido-substituted phenyl or phenacyl as illustrated herein.

For oral administration of compounds I-IV it is preferred that R$_1$ be

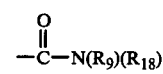

wherein R$_9$ and R$_{18}$ are as defined above, It is especially preferred that at least one of R$_9$ and R$_{18}$ be hydrogen.

As to variations in L, it is preferred that "$d$" be 2, 3, or 4, and especially 2. When both R$_2$'s are fluoro, it is preferred that R$_8$ in Q be methyl, or that R$_4$ be

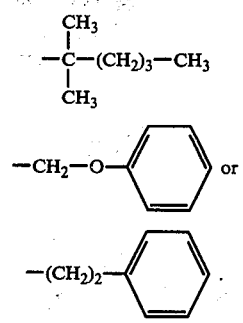

As to variations in (R$_{20}$), it is preferred that (R$_{20}$) be

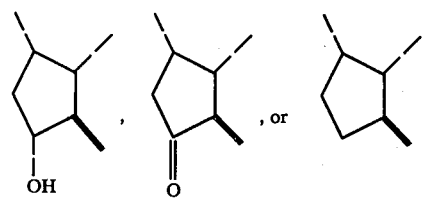

When R$_4$ in the compounds of formula I-IV is

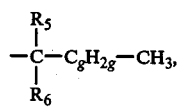

it is preferred that C$_g$H$_{2g}$ be alkylene of 2, 3, or 4 carbon atoms, and especially that it be trimethylene. It is further preferred that R$_5$ and R$_6$ be hydrogen, methyl, ethyl, or fluoro, being the same or different. It is further preferred, when R$_5$ and R$_6$ are not hydrogen, that both R$_5$ and R$_6$ be methyl or fluoro. It is especially preferred that R$_4$ be n-pentyl, 1,1-dimethylpentyl, or 1,1-difluoropentyl.

When R$_4$ in the compounds of formulas I-IV is

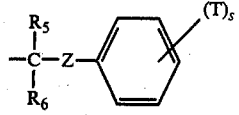

it is preferred that "s" be either zero or one. When "s" is not zero, it is preferred that T be methyl, chloro, fluoro, trifluoromethyl, or methoxy with meta or para attachment to the phenyl ring. When Z is oxa (—O—), it is preferred that $R_5$ and $R_6$ be hydrogen, methyl, or ethyl, being the same or different. It is further preferred, when $R_5$ and $R_6$ are not hydrogen, that both $R_5$ and $R_6$ be methyl. When Z is $C_jH_{2j}$, it is preferred that $C_jH_{2j}$ be a valence bond, methylene, or ethylene. It is especially preferred that $R_4$ be

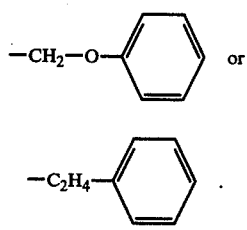

There are herein provided the various processes for preparing the 6-keto compounds of formula I, the 6-hydroxy (hemi-ketal) compounds of formula II, the 5-halo compounds of formula III, and the $PGI_2$-type (enol ether) compounds of formula IV.

Thus, for the formula-I, -II, and -III compounds one process comprises the steps of starting with a compound of the formula

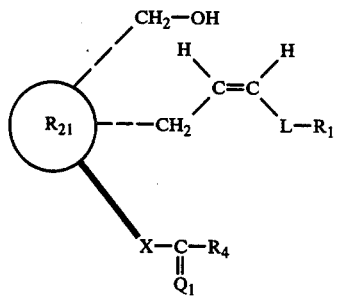

wherein L, $Q_1$, $R_1$, $R_4$, $(R_{21})$, and X are as defined above, and (a) halogenating and cyclizing to form a compound of the formula

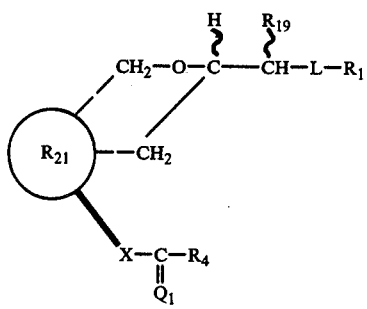

wherein L, $Q_1$, $R_1$, $R_4$, $R_{19}$, $(R_{21})$, X, and ~ are as defined above, (b) subjecting the product of step "a" to dehalogenation and hydrolysis to form to keto compound of the formula

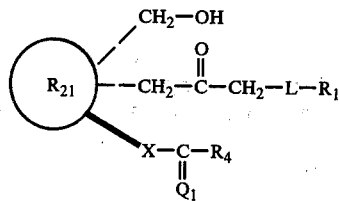

and a hemi-ketal compound of the formula

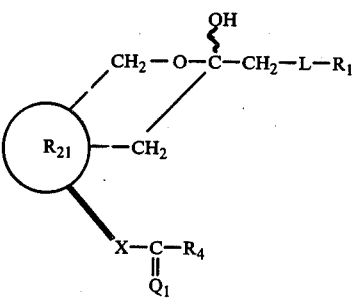

wherein L, $Q_1$, $R_1$, $R_4$, $(R_{21})$, X, and ~ are as defined above, and, when $R_{13}$ in $(R_{21})$ or $Q_1$ is not hydrogen, (c) replacing the blocking groups of $R_{13}$ with hydrogen to yield

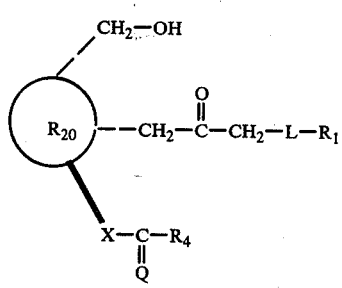

and

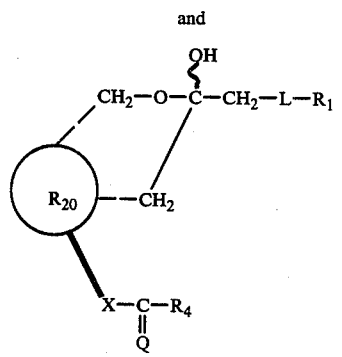

and (d) separating the products.

The symbol $(R_{21})$ includes all of the ring systems of the symbol $(R_{20})$ defined above, together with those in which there is a blocking group as defined by and within the scope of $R_{13}$ at C-11. The compounds produced, as represented by formulas X and XI, are inclusive of the formula-I and -II compounds together with those in which there is a blocking group retained from the formula-IX starting material. The compounds with blocking groups are useful as intermediates in further transformations of the formula-III, -X, and -XI compounds.

An alternate process for the formula-I and -II compounds is by starting with a formula-IV compound (to be discussed below) and subjecting it to acid hydrolysis. If that formula-IV compound has blocking groups, e.g. if it is a 11,15-bis (tetrahydropyran-2-yl) ether, those blocking groups are replaced with hydrogen by methods known in the art.

For the formula-IV enol ethers, the process employs dehydrohalogenation of the formula-III halo compounds. Accordingly, the process comprises the steps of starting with a compound of the formula

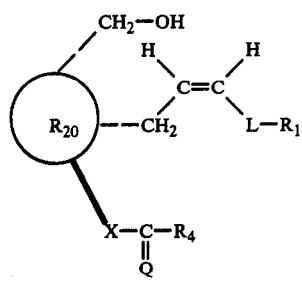

XII wherein L, Q, $R_1$, $R_4$, $R_{20}$ and X are as defined above, and (a) transforming that compound to a halo compound of the formula

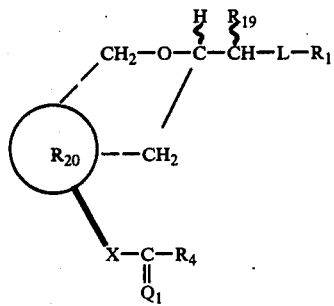

XIII wherein L, Q, $R_1$, $R_4$, $R_{19}$, $R_{20}$ and X are as defined above, (b) subjecting the product of step "a" to dehydrohalogenation with a tertiary amine or a reagent selected from the group consisting of sodium or potassium superoxide, sodium or potassium carbonate, sodium or potassium hydroxide, sodium or potassium benzoate, sodium or potassium acetate, sodium or potassium trifluoroacetate, sodium or potassium bicarbonate, silver acetate, and a tetraalkylammonium superoxide of the formula $(R_{12})_4NO_2$ wherein $R_{12}$ is alkyl of one to 4 carbon atoms, inclusive to form the enol ethers; and (c) separating the products.

Reference to Chart A, herein, will make clear the steps for preparing the formula-I, -II, and -III compounds disclosed herein.

In Chart A, the terms L, Q, $Q_1$, $R_1$, $R_4$, $R_{19}$, $R_{20}$, $R_{21}$, X and ~ have the same meanings as defined above.

Examples of alkyl of one to 4 carbon atoms, inclusive, are methyl, ethyl, propyl, butyl, and isomeric forms thereof. Examples of alkyl of one to 7 carbon atoms, inclusive, are, in addition, pentyl, hexyl, heptyl, and isomeric forms thereof. Examples of alkyl of one to 12 carbon atoms, inclusive, are, in addition, octyl, nonyl, decyl, undecyl, dodecyl, and isomeric forms thereof. Examples of alkyl of one to 18 carbon atoms are, in addition, tridecyl, tetradecyl, pentadecyl, hexadecyl, heptadecyl, octadecyl, and isomeric forms thereof.

Examples of cycloalkyl of 3 to 10 carbon atoms, inclusive, which includes alkyl-substituted cycloalkyl, are cyclopropyl,
2-methylcyclopropyl,
2,2-dimethylcyclopropyl,
2,3-diethylcyclopropyl,
2-butylcyclopropyl
cyclobutyl,
2-methylcyclobutyl,
3-propylcyclobutyl,
2,3,4-triethylcyclobutyl,
cyclopentyl,
2,2-dimethylcyclopentyl,
3-pentylcyclopentyl,
3-tert-butylcyclopentyl,
cyclohexyl,
4-tert-butylcyclohexyl,
3-isopropylcyclohexyl,

CHART A

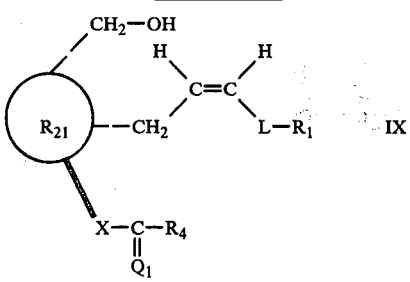

IX (a)

CHART A

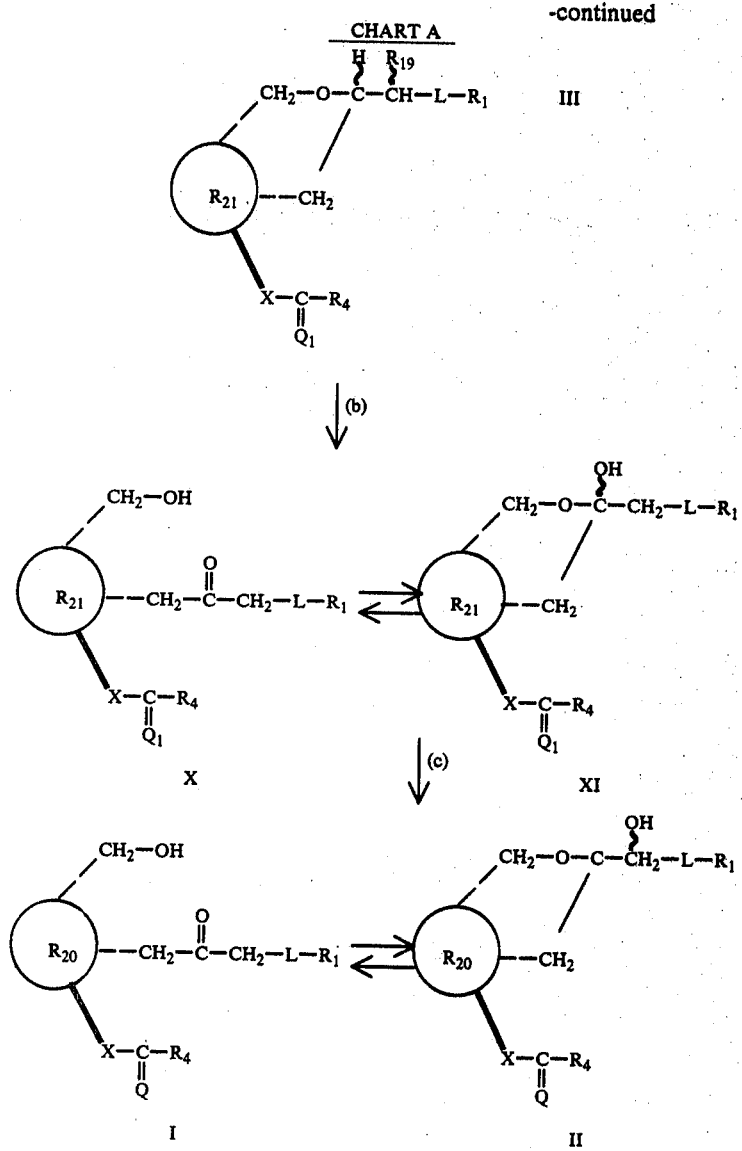

2,2-dimethylcyclohexyl,
cycloheptyl,
cyclooctyl,
cyclononyl,
and cyclodecyl.

Examples of phenylalkyl of 7 to 10 carbon atoms, inclusive, are
benzyl,
1-phenylethyl,
2-phenylethyl,
2-phenylpropyl,
4-phenylbutyl, and
3-phenylbutyl.

Examples of aralkyl of 7 to 12 carbon atoms, inclusive, are, in addition
2-(1-naphthylethyl),
and 1-(2-naphthylmethyl).

Examples of phenyl substituted by one to 3 chloro or alkyl of one to 4 carbon atoms, inclusive are
p-chlorophenyl,
m-chlorophenyl,
o-chlorophenyl,
2,4-dichlorophenyl,
2,4,6-trichlorophenyl,
p-tolyl,
m-tolyl,
o-tolyl,
p-ethylphenyl,
p-tert-butylphenyl,
2,5-dimethylphenyl,
4-chloro-2-methylphenyl,
and 2,4-dichloro-3-methylphenyl.

Examples of alkylene of one to 9 carbon atoms, inclusive, with one to 5 carbon atoms, inclusive, in the chain, within the scope of $C_gH_{2g}$ as defined above, are methylene, ethylene, trimethylene, tetramethylene, and pentamethylene, and those alkylene with one or more alkyl substitutuents on one or more carbon atoms thereof, e.g. $-CH(CH_3)-$, $-C(CH_3)_2-$, $-CH(CH_2CH_3)-$, $-CH_2-CH(CH_3)-$, $-CH(CH_3)-$, $-CH_2-C(CH_3)_2-$, $-CH_2-CH(CH_3)-CH_3-$, $-CH_2-CH-2-CH(CH_2CH_2CH_3)-$, $-CH(CH_3)-CH(CH_3)-CH_2-CH_2-$, $-CH_2-CH_2-CH_2-C(CH_3)_2-CH_2$, and $-CH_2-CH_2-CH_2-CH_2-CH(CH_3)-$. Examples of alkylene of one to 9 carbon atoms, inclusive, substituted with zero, one, or 2 fluoro, with one to 6 carbon atoms in the chain, within the scope of $C_jH_{2j}$ as defined above, are those given above for $C_gH_{2g}$ and hexamethylene, including hexamethylene with one or more alkyl substituents on one of more carbon atoms thereof, and including those alkylene groups with one or 2 fluoro substituents on one or 2 carbon atoms thereof, e.g. —CHF—CH$_2$—, —CHF—CHF—, —CH$_2$—CH$_2$—CF$_2$—, —CH$_2$—CHF—CH$_2$—, —CH$_2$—CH$_2$—CF (CH$_3$)—, —CH$_2$—CH$_2$—CF$_2$—CH$_2$—, —CH(CH$_3$)—CH$_2$—CH$_2$—CHF—, —CH$_2$—CH$_2$—CH$_2$—CH$_2$—CF$_2$—, —CHF—CH$_2$—CH$_2$—CH$_2$—CH$_2$—CHF—, —CF$_2$—CH$_2$—CH$_2$—CH$_2$—CH$_2$—, —CH$_2$—CH$_2$—CH$_2$—CF$_2$—CH$_2$—CH$_2$—, and —CH$_2$—CH$_2$—CH$_2$—CH$_2$—CH$_2$—CF$_2$.

Examples of

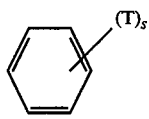

as defined above are
phenyl,
(o-, m-, or p-)tolyl,
(o-, m-, or p-)ethylphenyl,
(o-, m-, or p-)propylphenyl,
(o-, m-, or p-)butylphenyl,
(o-, m-, or p-)isobutylphenyl,
(o-, m-, or p-)tert-butylphenyl,
2,3-xylyl,
2,4-xylyl,
2,5-xylyl,
2,6-xylyl,
3,4-xylyl,
2,6-diethylphenyl,
2-ethyl-p-tolyl,
4-ethyl-o-tolyl,
5-ethyl-m-tolyl,
2-propyl-(o-, m-, or p-)tolyl,
4-butyl-m-tolyl,
6-tert-butyl-m-tolyl,
4-isopropyl-2,6-xylyl,
3-propyl-4-ethylphenyl,
(2,3,4-, 2,3,5-, 2,3,6-, or 2,4,5-)trimethylphenyl,
(o-, m-, or p-)fluorophenyl, 2-fluoro-(o-, m-, or p-)tolyl,
4-fluoro-2,5-xylyl,
(2,4-, 2,5-, 2,6-, 3,4-, or 3,5-)difluorophenyl,
(o-, m-, or p-)chlorophenyl,
2-chloro-p-tolyl,
(3-, 4-, 5-, or 6-)chloro-o-tolyl,
4-chloro-2-propylphenyl,
2-isopropyl-4-chlorophenyl,
4-chloro-3,5-xylyl,
(2,3-, 2,4-, 2,5-, 2,6-, 3,4-, or 3,5-)dichlorophenyl,
4-chloro-3-fluorophenyl,
(3-, or 4-)chloro-2-fluorophenyl,
α,α,α-trifluoro-(o-, m-, or p-)tolyl,
(o-, m-, or p-)methoxyphenyl,
(o-, m-, or p-)ethoxyphenyl,
(4- or 5-)chloro-2-methoxyphenyl, and
2,4-dichloro(5- or 6-))methoxyphenyl.

Included in this invention are the pharmacologically acceptable salts when $R_1$ is hydrogen. Pharmacologically acceptable salts of these formula I-IV compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phentylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galacetamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

Included in the compounds of this invention are the lower alkanoates, wherein "lower alkanoate" refers to an ester of an alkanoic acid of one to 8 carbon atoms, inclusive. Examples of such alkanoic acids are formic, acetic, propanoic, butanoic, pentanoic, hexanoic, heptanoic, and octanoic acids, and isomeric forms thereof.

Referring to chart A, the starting materials of formula IX are 9-deoxy-9α-hydroxymethyl derivatives of PGF$_2$-type compounds known in the art or readily available by processes known in the art. See especially U.S. Pat. No. 3,950,363 as to general methods, and as to 9-deoxy-9α-hydroxymethyl-PGF$_2$, methyl ester, and free acid, and analogs, at columns 14–18, and 34–42, which are incorporated herein by reference. The method of preparation, stated briefly, is to start with a PGE$_2$-type compound previously blocked with silyl groups at C-11 and C-15, and replace the 9-oxo groups with 9-methylene by reaction with a carbanion of an N-alkyl, S-methyl-S-aryl sulfoximine followed by aluminumamalgam reduction, then to block again at C-11 and C-15 with silyl groups, and to transform the 9-methylene group by hydroboration-oxidation to a hydroxymethyl group.

Consequently, the ultimate starting materials for the intermediates of Chart A are PGE$_2$-type compounds which are transformed to the 9-deoxy-9α-hydroxymethyl-PGF$_2$-type compounds of formula IX. Those PGE$_2$-type compounds are within the scope of formula XXVI:

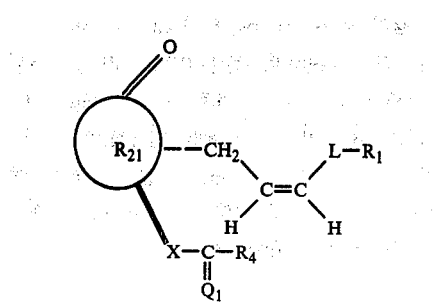

XXVI wherein L, $Q_1$, $R_1$, $R_4$, $R_{21}$, and X are as defined above. For example, as to $PGE_2$, see U.S. Pat. No. 3,598,858; as to 15-methyl-$PGE_2$, see U.S. Pat. No. 3,812,179; as to 15(R)-15-methyl-$PGE_2$, see U.S. Pat. No. 3,804,889; as to $PGE_2$ esters see U.S. Pat. No. 3,795,697 and 3,691,216; as to 17,18-didehydro-$PGE_2$, see U.S. Pat. No. 3,598,858; as to 16- and 16,16-dimethyl-$PGE_2$, see U.S. Pat. No. 3,903,131; as to 3-oxa-$PGE_2$, see U.S. Pat. No. 3,944,953; as to 4-oxa-$PGE_2$, see U.S. Pat. No. 3,920,723; as to 3-oxa-17-phenyl-18,19,20-trinor-$PGE_2$, see U.S. Pat. No. 3,931,289; as to $PGE_2$, 15-alkyl ethers, see U.S. Pat. Nos. 3,835,180 and 3,781,325; as to 16- and 16,16-difluoro-$PGE_2$, see U.S. Pat. No. 3,974,189; as to 11$\beta$-$PGE_2$, see U.S. Pat. No. 3,931,284; as to 15$\beta$-$PGE_2$, see U.S. Pat. No. 3,880,912; as to substituted phenyl esters of $PGE_2$, see U.S. Pat. No. 3,894,062; as to 2a,2b-dihomo-$PGE_2$ compounds, see U.S. Pat. Nos. 3,852,316 and 3,974,195; as to 16-phenoxy-17,18,19,20-tetranor-$PGE_2$, see Derwent Farmdoc No. 73279U and British Spec. No. 1,409,841; as to 17-phenyl-18,19,20-trinor-$PGE_2$, see U.S. Pat. No. 3,987,087; as to 11-deoxy-$PGE_2$, see Derwent Farmdoc No. 10695V and British Spec. No. 1,434,620; as to substituted phenacyl esters, see Derwent Farmdoc No. 16826X and U.S. Pat. No. 3,979,440; as to 2-decarboxy-2-hydroxymethyl compounds, see U.S. Pat. No. 3,636,120; as to C-2 tetrazolyl derivatives, see U.S. Pat. Nos. 3,883,513 and 3,932,389; as to $\Delta_2$-$PGE_2$, see Derwent Farmdoc No. 46497W and German Offenlegungsschrift 2,460,285; as to 11-deoxy-11-hydroxymethyl-$PGE_2$, see U.S. Pat. No. 3,931,282; as to 3-(or 4-)oxa-17,18-didehydro-$PGE_2$ compounds, see U.S. Pat. Nos. 3,931,289 and 3,996,266; as to 15-deoxy-$PGE_2$, see Derwent Farmdoc No. 9239W; as to 11-deoxy-15-deoxy-$PGE_2$, see U.S. Pat. No. 3,853,951; as to 13-cis-$PGE_2$, see U.S. Pat. No. 3,932,479; as to 13,14-didehydro-$PGE_2$, see Derwent Farmdoc No. 20717X; as to 2,2-difluoro-$PGE_2$, see U.S. Pat. No. 4,001,300; and as to 11$\beta$-17-phenyl-18,19,20-trinor-$PGE_2$, see Derwent Farmdoc No. 13090X.

As to 2-decarboxy-2-aminomethyl-$PGF_{2\alpha}$ compounds, see Preparation 2 herein, which illustrates a sequence of reactions useful not only in preparing starting materials for Chart A but, preferably, also useful in producing end products wherein the $R_1$ group is aminomethyl.

As to compounds of formula IX with ether-bonded blocking groups such as tetrahydropyranyl or ethoxyethyl and others within the scope of $R_{13}$, see for example Corey et al., J. Am. Chem. Soc. 92, 397 (1970) and the sources cited above. When $R_{13}$ is carboxyacyl, for example benzoyl, it is preferred that such groups be introduced on the halo compound III using methods known in the art. Thus benzoyl chloride is reacted with the formula-III compound in the presence of a tertiary amine such as pyridine at 20°-60° C. in an inert solvent such as benzene, toluene or chloroform. See U.S. Pat. No. 3,778,450. Likewise blocking groups such as tetrahydropyranyl and ethoxyethyl may be introduced on the halo compound III by methods known in the art. For tetrahydropyranyl groups, for example, 2,3-dihydropyran is used in an inert solvent such as methylene chloride at 20°-50° C. in the presence of an acid condensing agent such as p-toluenesulfonic acid. See U.S. Pat. No. 3,944,593.

In step "a" of Chart A, the starting material IX is subjected to halogenation and cyclization to yield the formula-I halo compounds. For this purpose there are various methods available. For the iodo compounds there may be used an aqueous system containing iodine, potassium iodide, and an alkali carbonate or bicarbonate, or or organic solvent system such as dichloromethane containing iodine in the presence of an alkali metal carbonate. The reaction is carried out at temperatures below 25° C., preferably about 0°-5° C. for 10-20 hours. Thereafter the reaction is quenched with sodium sulfite and sodium carbonate and the formula-III compound separated from the reaction mixture.

For the bromo compounds, N-bromosuccinimide or N-bromoacetamide are useful. See Fieser et al., Reagents for Organic Synthesis, Vol. 1, pp. 74 and 78, Vol. IV, p. 51, John Wiley and Sons, Inc., N.Y. for the chloro compound various methods are available, for example exchange of bromo with chloro with the silver salt of chlorodifluoroacetic acid. See I. T. Harrison et al., Compendium of Organic Synthetic Methods, p. 346, 1971, Wiley Interscience, N.Y.

The formula-I halo compounds are obtained as two isomers, one in minor and the other in major quantity, differing in their chromatographic mobility.

Structures for the iodo ethers derived from 9-deoxy-9$\alpha$-hydroxymethyl-$PGF_2$, methyl ester, for example, are believed to be:

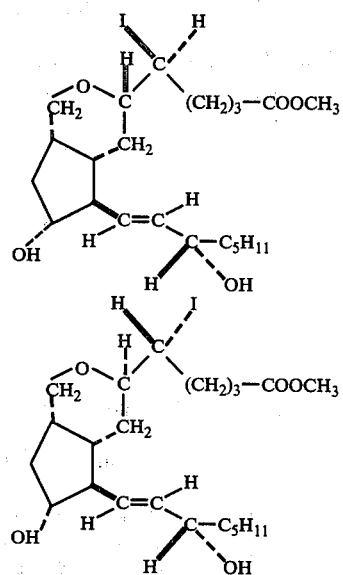

These C-5 and C-6 isomers are separable by silica gel chromatography, yielding on elution, e.g. with methylene chloride (15-50%)-acetone, first the less polar, formula-XIX (5S,6S) isomer in about 8% of the total, and, second, the more polar, formula-XX (5R,6R) isomer.

Normally these isomers need not be separated, as either one yields the desired products in step (b) of Chart A.

In step "b" of Chart A the halo compound III is converted to an equilibrium mixture of the 6-keto compound X and the 6-hydroxy compound XI by contacting with silver carbonate and perchloric acid. The reaction is done in an inert organic medium such as tetrahydrofuran and is followed with TLC to determine completion, normally in 15–24 hours at about 25° C. The reaction is preferably done in absence of light.

Although the product of step "b" normally contains compounds X and XI, further equilibrium may be accomplished merely by preparing a solution of that product in an organic solvent, e.g. acetone or dichloromethane, and letting it stand for several days. The resulting mixture is concentrated and separated, for example by silica gel chromatography.

In optical step "c" of Chart A, the products of step "b" are freed by blocking groups within the scope of $R_{13}$ if present from the initial starting materials of formula IX, to yield the formula-I and -II compounds. For this purpose methods known in the art are used, for example mild acid hydrolysis for tetrahydropyranyl and similar ether-bonded groups, using dilute acetic acid, aqueous citric acid, or aqueous phosphoric acid in a mutual solvent such as tetrahydrofuran. For carboxyacylates, mild deacylating agents are used, for example potassium carbonate in methanol at about 25° C.

Still another route to the mixture of 6-keto and hemiketal compounds I and II is by treating the formula-III halo compound in alcoholic solution, e.g. methanol, with aqueous alkali metal hydroxide, e.g. potassium hydroxide, at a temperature in the range of 0° to 30° C. for several hours. After acidification there is obtained a mixture of the acid form of the formula-III compound and the formula-XI hemi-ketal together with some of the formula-X 6-keto compound, which are separated, for example, by silica gel chromatography or by fractional crystallization. Any remaining blocking groups $R_{13}$ are removed in the conventional way.

The formula I and II compounds, separately or as a mixture, are converted to a 6ξ-methoxy ketal of the formula

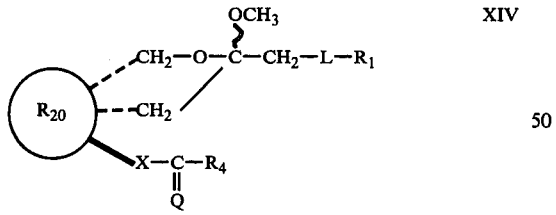

either on long contact with methanol or by methylation with diazomethane. These ketal compounds have pharmacological activity but are not the subject of this invention.

Considering the scope of $R_1$ in products of formula I and II, there are included acids, esters, 2-decarboxy-2-hydroxymethyl compounds, 2-decarboxy-2-aminomethyl compounds, amides, and 2-decarboxy-2-tetrazolyl compounds. To prepare any of these derivatives, the procedure of Chart A is adaptable. For example, for the esters, either the starting material IX or the halo compound III is prepared as an ester and thereafter converted to the formula I and II esters. Methods of preparing esters are known in the art, including esterification with diazohydrocarbons, and interaction of a silver salt of the prostaglandin derivative with an alkyl iodide. For phenacyl-type esters the acid prostaglandin derivative is reacted with the phenacyl bromide, for example p-phenylphenacyl bromide, in the presence of a tertiary amine. See German Offenlegungsschrift No. 2,535,693 cited above. For substituted phenyl esters see U.S. Pat. No. 3,890,372.

A preferred method of preparing amides of formulas

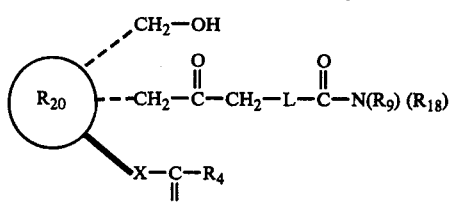

XV

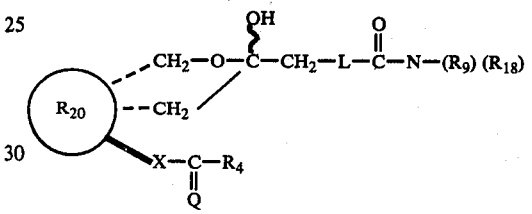

XVI is by the steps shown in Chart B. In Chart B, the terms L, Q, $R_4$, $R_9$, $R_{18}$, $R_{19}$, $R_{20}$, X and - have the same

CHART B

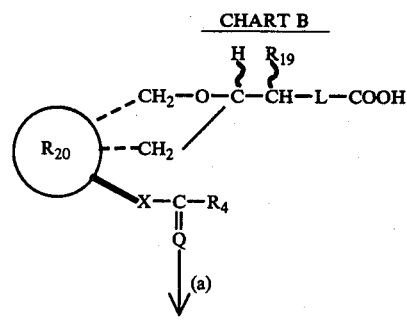

XVII

↓(a)

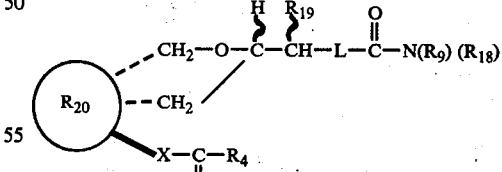

XVIII

↓(b)

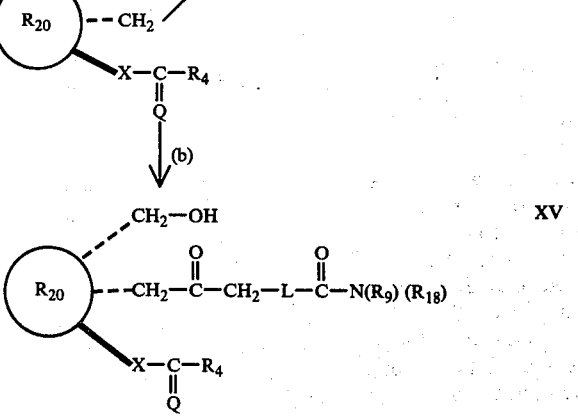

XV

-continued
CHART B

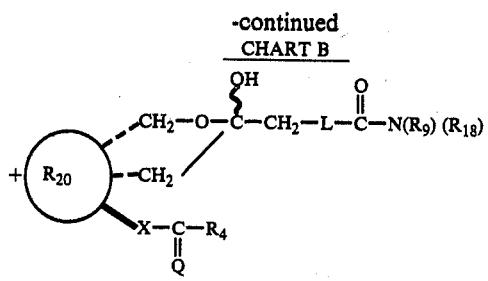

-continued
CHART C

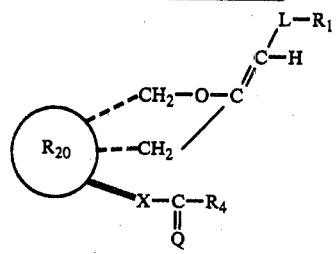   IV meanings as defined above.

Halo acid XVII is converted to amide XVIII, e.g. by way of a mixed anhydride. For this purpose, compound XVII is treated with isobutyl chloroformate in the presence of a tertiary amine such as triethylamine and thereafter with an amine of the formula $HN(R_9)(R_{18})$ wherein $R_9$ and $R_{18}$ are as defined herein. The halo amide XVIII is then subjected to dehydrohalogenation and hydrolysis as disclosed herein to form the mixed formula-XV and -XVI products. Optionally those products are separated, as by silica gel chromatography.

2-Decarboxy-2-hydroxymethyl compounds wherein $R_1$ in formulas I and II is $-CH_2OH$ are prepared from corresponding starting materials of formula IX.

Reference to Chart C herein will make clear the steps for preparing the formula-IV enol ethers. In Chart C the terms L, Q, $R_1$, $R_4$, $R_{19}$, $R_{20}$, X and $\sim$ are as defined for Chart A.

The starting materials XII are known in the art (see references cited above for Chart A) or are prepared by methods described herein or known in the art. They differ from the formula-IX compounds of Chart A in that they do not have blocking groups and thereby yield halo intermediates XIII and enol ethers IV free of blocking groups.

If enol ethers corresponding to formula IV but with

CHART C

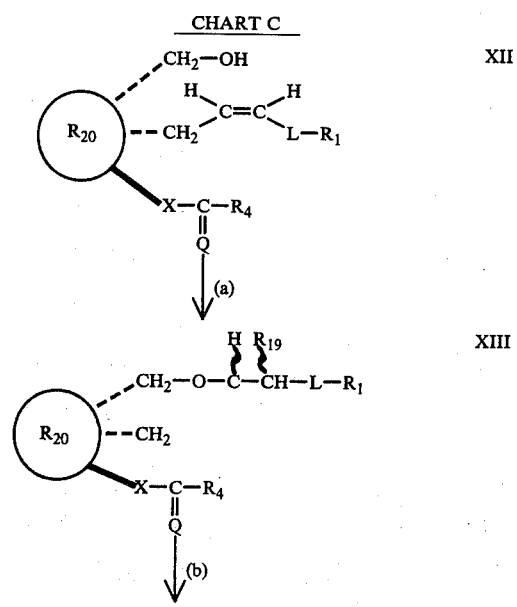

blocking groups are desired, as for transformation to other useful compounds, they are obtained by replacing compounds XII or XIII with suitably blocked compounds or by simply reacting the formula-IV compounds with suitable reagents. If the blocking groups are to be ultimately removed to yield a formula-IV type product, it is preferred that they be not ether-bonded groups such as tetrahydropyranyl which normally are removed by acid hydrolysis. Contact of a formula-IV type product with acid readily converts it to a 6-keto compound of formula I.

In step "a" of Chart C, the starting materials XII are subjected to halogenation or otherwise transformed to the halo compounds of formula XIII, as in Chart A, and as described above.

In step "b" of Chart C the halo compounds XIII is converted to the formula-IV enol ether compound by contacting it with a dehydrohalogenation reagent. For such reagents see, for example, Fieser and Fieser, "Reagents for Organic Synthesis" p. 1308, John Wiley and Sons, Inc., New York, N.Y. (1967). Preferred for the reaction of step "b" are tertiary amines and reagents selected from the group consisting of sodium or potassium superoxide, sodium or potassium carbonate, sodium or potassium hydroxide, sodium or potassium benzoate, sodium or potassium acetate, sodium or potassium trifluoroacetate, sodium or potassium bicarbonate, silver acetate, and a tetraalkylammonium superoxide of the formula $(R_{12})_4NO_2$ wherein $R_{12}$ is alkyl of one to 4 carbon atoms, inclusive.

Of the tertiary amines, preferred amines are 1,5-diazabicyclo[4.3.0]nonene-5 ("DBN"), 1,4-diazabicyclo[2.2.2]octane ("DABCO"), and 1,5-diazabicyclo[5.4.0]undecene-5 ("DBU").

Other preferred reagents are sodium or potassium superoxide and tetramethylammonium superoxide. For further information on the superoxides see Johnson and Nidy, J. Org. Chem. 40, 1680 (1975). For larger scale preparation the electrochemical generation of superoxide is recommended. See Dietz et al., J. Chem. Soc. (B), 1970, pp. 816–820.

The dehydrohalogenation step is carried out in an inert organic medium such as dimethylformamide and is followed by TLC to show the disappearance of starting material. The reaction proceeds at 25° C. and can be accelerated at 40°-50° C.

In working up the reaction mixture it is advantageous to maintain basic conditions, e.g. with trimethylamine, to avoid acidic decomposition or structural changes of the product. Purification is achieved by crystallization and consequent separation from impurities or starting material left in the mother liquor, or by column chromatography. For chromatographic separation a column of magnesium silicate ("Florisil ®") is preferred over silica gel. Decomposition of the product is avoided by pretreating the column with triethylamine.

Ester groups such as the p-phenylphenacyl group on the C-1 carboxyl or 4-bromobenzoate on C-11 and C-15 hydroxyls are unchanged by the transformations of Chart C, and, if present on the formula-XII starting material, are also present on the formula-IV product. For the final products of formula IV which are esters the preferred method of preparation is from formula-XIII halo compounds which are corresponding esters.

Esters of the formula-XII and -IV compounds are prepared by methods known in the art. Using the corresponding acids of such compounds, the alkyl, cycloalkyl, and aralkyl esters are prepared by interaction of said acids with the appropriate diazohydrocarbon. For example, when diazomethane is used, the methyl esters are produced. Similar use of diazoethane, diazobutane, 1-diazo-2-ethylhexane, diazocyclohexane, and phenyldiazomethane, for example, gives the ethyl, butyl, 2-ethylhexyl, cyclohexyl, and benzyl esters, respectively. Of these esters, the methyl or ethyl are preferred.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley and Sons, Inc., New York, N.Y., Vol. 8, pp. 389-394 (1954).

Substituted phenyl esters of the formula-XII and -XIII compounds are prepared by methods known in the art. See for example U.S. Pat. No. 3,890,372. A preferred process is by reacting a mixed anhydride with an appropriate phenol or naphthol. The anhydride is formed with isobutylchloroformate in the presence of a tertiary amine.

Phenyl and substituted phenyl esters of the formula-XII and -XIII compounds are also prepared by silylating the acid to protect the hydroxy groups, for example, replacing each —OH with —O—Si—$(CH_3)_3$. Doing that may also change —COOH to —COO—Si—$(CH_3)_3$. A brief treatment of the silylated compound with water will change —COO—Si—$(CH_3)_3$ back to —COOH. Procedures for this silylation are known in the art and are discussed hereinafter. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—$(CH_3)_3$ are changed back to —OH by treatment with dilute acetic acid. Procedures for these transformations are known in the art.

The formula I, II, and IV compounds prepared by the processes described herein are transformed to lower alkanoates by interaction with a carboxyacylating agent, preferably the anhydride of a lower alkanoic acid, i.e., an alkanoic acid of one to 8 carbon atoms, inclusive. For example, use of acetic anhydride gives the corresponding diacetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 1,000 moles of anhydride per mole of the hydroxy compound reactant. The excess anhydride serves as a reaction diluent and solvent. An inert organic diluent, for example dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride. For acetic anhydride, pyridine, and a 25° C. reaction temperature, a 12-to-24 hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxylate is recovered from the diethyl ether extract by evaporation. The carboxylate is then purified by conventional methods, advantageously by chromatography.

Alternatively, and preferably, a starting material of formula IX or XII or a halo intermediate of formula III or XIII is carboxyacylated and thereafter transformed to a formula-I, -II, or -IV product.

Salts of these formula-I, -II and -IV compounds are prepared with pharmacologically acceptable metal cations, ammonium, amine cations, or quaternary ammonium cations. Several methods are employed, for example using either the formula-IX or -XII starting materials in their salt form or, when considered as intermediates in preparing the formula-I, -II, and -IV products, the formula-III compounds in their salt form. In addition, the free acids may be prepared by careful acidification of a soluble alkali metal salt of a formula I, II or IV compound and rapid extraction into an organic solvent to avoid prolonged contact with an acidic aqueous medium; thereupon the desired salt may be prepared from the stoichiometric amount of hydroxide, carbonate, or bicarbonate in the case of metal cations, or the amine or hydroxide in the case of other salts.

Especially useful for administration because of their form as free-flowing powders and their ease of dissolving are sodium salts. They are obtained from formula-IV esters, preferably methyl or ethyl, by saponification with equivalent amounts of sodium hydroxide in a solvent, preferably an alcohol-water solution, thereafter lyophilizing (freeze-drying) the mixture to obtain the powdered product. Alternatively, excess amounts of sodium carbonate are used instead of sodium hydroxide.

As discussed above, the compounds of formula I, III, and IV are administered in various ways for various purposes; e.g., intravenously, intramuscularly, subcutaneously, orally, intravaginally, rectally, buccally, sublingually, topically, and in the form of sterile implants for prolonged action.

For intravenous injection or infusion, sterile aqueous isotonic solutions are preferred. For that purpose, it is preferred because of increased water solubility that $R_3$ in the formula I, II, and IV compounds be hydrogen or a pharmacologically acceptable cation. For subcutaneous or intramuscular injection, sterile solutions or suspensions of the acid, salt, or ester form in aqueous or nonaqueous media are used. Tablets, capsules, and liquid preparations such as syrups, elixirs, and simple solutions, with the usual pharmaceutical carriers are used for oral sublingual administration. For rectal or vaginal administration suppositories prepared as known in the art are used. For tissue implants, a sterile tablet or silicone rubber capsule or other object containing or impregnated with the substance is used.

This invention also includes the 1,15-lactones obtained from the formula-III compounds wherein $R_1$ is —COOH and Q is

for example
9-deoxy-6,9α-epoxymethano-5-iodo-PGF$_1$, 1,15-lactone.

For their preparation, analogous methods are used to those disclosed in German Offenlegungsschrift No. 2,627,671 and U.S. Pat. No. 4,032,543.

It should be understood that although the Charts have formulas drawn with a specific configuration for the reactants and products, the procedural steps are intended to apply not only to the other optically active isomers, but also to mixtures, including racemic mixtures or mixtures of enantiomeric forms.

If optically active products are desired, optically active starting materials or intermediates are employed or, if racemic starting materials or intermediates are used, the products are resolved by methods known in the art for prostaglandins.

The products formed from each step of the reaction are often mixtures and, as known to one skilled in the art, may be used as such for a succeeding step or, optionally, separated by conventional methods for fractionation, column chromatography, liquid-liquid extraction, and the like, before proceeding.

Compounds within the scope of formula I, II, III or IV are transformed from one to another by methods known in the art. Accordingly, the compound of formula V, a compound within the scope of formula I wherein 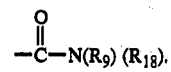 is

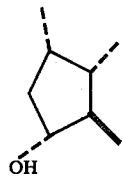

is transformed to another formula-I compound wherein $R_{20}$ is another ring within the scope of $R_{20}$, for example an 11-deoxy compound, by methods known or described herein. A compound wherein the $C_{13}$-$C_{14}$ is trans—CH=CH— is transformed by known methods to another compound wherein the $C_{13}$-$C_{14}$ group is cis—CH=CH—, —C≡C—, or —CH$_2$CH$_2$—. For example, —C≡C— is obtained by selective bromination and dehydrobromination. A compound wherein the $C_2$ substituent is —COOR, e.g. a methyl ester, is transformed by known methods to another compound having another $C_2$ substituent within the scope of $R_1$ as defined herein, for example —CH$_2$OH or $$-\overset{O}{\underset{\|}{C}}-N(R_9)(R_{18}).$$

Also included within the scope of this invention are compounds of the formula

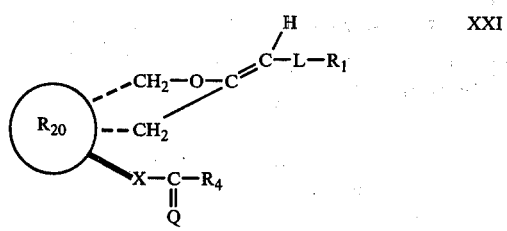

wherein L, Q, $R_1$, $R_4$, $R_{20}$, and X are as defined herein.

There are likewise provided compounds of the formula

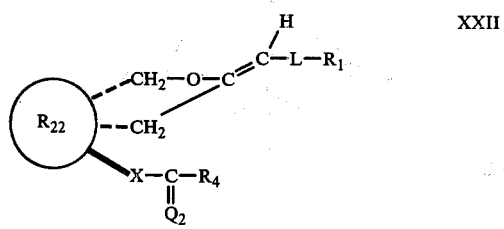

wherein L, $R_1$, $R_4$, and X have the same meanings as in XXI, and wherein $R_{20}$ is

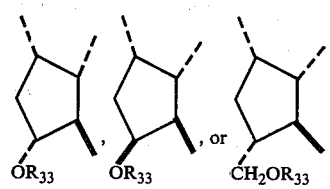

wherein $K_{33}$ is (a) tetrahydropyranyl, (b) tetrahydrofuranyl, (c) 1-ethoxyethyl, (d) a group of the formula

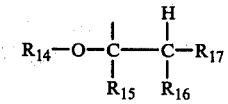

wherein $R_{14}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{15}$ and $R_{16}$ are the same or different, being hydrogen, alkyl of one to 4 carbon atoms, inclusive, phenyl or phenyl substituted with one, 2, or 3 alkyl of one to 4 carbon atoms, inclusive, or, when $R_{15}$ and $R_{16}$ are taken together, —(CH$_2$)a— or —(CH$_2$)b—O—(CH$_2$)c— wherein $a$ is 3, 4, or 5, $b$ is one, 2, or 3, and $c$ is one, 2, or 3 with the proviso that $b$ plus $c$ is 2, 3, or 4, and wherein $R_{17}$ is hydrogen or phenyl, or (e) carboxyacyl including

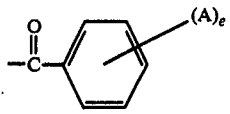 (a')

wherein "A" is alkyl of one to 4 carbon atoms, inclusive, bromo, phenylalkyl of 7 to 10 carbon atoms, inclusive, or nitro, and "e" is zero to 5, inclusive, provided that not more than two A's are other than alkyl, and that the total number of carbon atoms, in the A's does not exceed 10 carbon atoms.

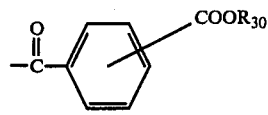 (b')

wherein $R_{30}$ is alkyl of one to 4 carbon atoms, inclusive,

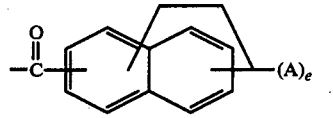 (c')

wherein "A" and "e" are as defined above, or

 (d')

wherein $R_{31}$ is alkyl of one to 7 carbon atoms, inclusive, and wherein $Q_2$ is

wherein $R_8$ is hydrogen or alkyl of one to 4 carbon atoms, inclusive, and $R_{33}$ is as defined above, Compounds so-defined are named as (5E) compounds following the Blackwood convention cited above. As examples of the formula-XXI and -XXII compounds, there are the compounds of formula XXIII and XXIV, respectively:

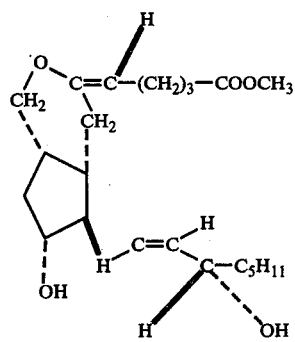 XXIII

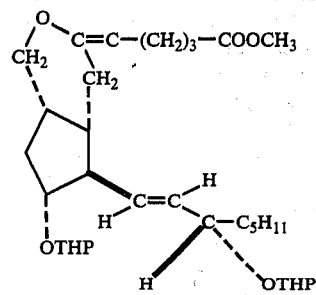 XXIV named (5E)-9-deoxy-6,9α-epoxymethano-Δ$^5$-PGF$_1$, methyl ester and (5E)-9-deoxy-6,9α-epoxymethano-Δ$^5$-PGF$_1$, methyl ester, bis(tetrahydropyranyl)ether.

These compounds of formula XXI are prepared analogously to those of formula IV by following the procedures described herein, especially referring to Chart C and the Examples related thereto, but replacing the formula-XII starting materials with corresponding 5,6-trans compounds represented by the formula

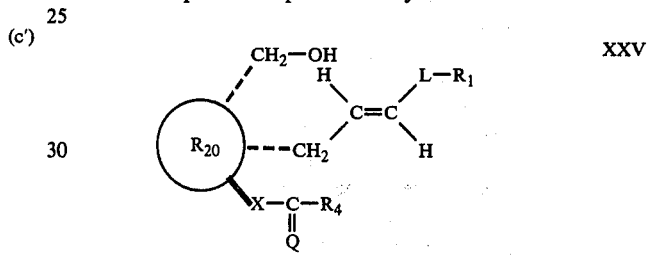 XXV

These compounds of formula XXV are known in the art or readily available by processes known in the art. For example, the processes described above for the 9-deoxy-9α-hydroxymethyl derivatives of PGF$_2$-type compounds starting with PGE$_2$-type compounds are applied to the corresponding 5,6-trans-PGE$_2$-type compounds. As to 5,6-trans-PGE$_2$, see for example U.S. Pat. No. 3,759,978.

Other 5,6-trans-PGF$_{2\alpha}$ analogs and derivatives within the scope of formula XXV are available from the corresponding formula-XII compounds described herein by isomerization utilizing ultraviolet radiation of the 5,6-cis compounds in the presence of a diaryl sulfide or disulfide, followed by separation. See the above-cited U.S. Pat. No. 3,759,978.

Compounds of formula XXIII are useful for pharmacological purposes, each one being useful in place of the known prostaglanin- or prostacyclin-type compounds for at least one of the pharmacological purposes described herein.

Compounds of formula XXII are prepared by blocking the hydroxyl group at C-11 and C-15 with blocking groups within the scope set forth herein. This may be done either at early stages in the synthesis as on the formula-XXV starting materials, or on the end products of formula XXI. Compounds of formula XXII have utility as intermediates.

DESCRIPTION OF THE PREFERRED EMBODIMENTS

The invention is further illustrated by, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60, A-60D, T-60 or XL-100 spectrophotometer in deuterochloroform solutions with tetramethylsilane as an internal standard.

Mass spectra are recorded on a Varian Model MAT CH7 Mass Spectrometer, a CEC Model 110B Double Focusing High Resolution Mass Spectrometer, or an LKB Model 9000 Gas Chromatograph-Mass Spectrometer (ionization voltage 22 or 70 ev.), and samples are usually run as TMS (trimethylsilyl) derivatives.

"Brine", herein, refers to an aqueous saturated sodium chloride solution.

"DBN", herein, refers to 1,5-diazabicyclo[4.3.0]nonene-5.

"DABCO", herein, refers to 1,4-diazabicyclo[2.2.2]octane.

"DBU", herein, refers to 1,5-diazabicyclo[5.4.0]undecene-5.

"E" and "Z", herein, follow Blackwood et al., cited above.

"Florisil®", herein, is a chromatographic magnesium silicate produced by the Floridin Co. See Fieser et al. "Reagents for Organic Synthesis" p. 393 John Wiley and Sons, Inc., New York, N.Y. (1967).

"TLC", herein, refers to thin layer chromatography.

Silica gel chromatography, as used herein, is understood to include elution, collection of fractions, and combinations of those fractions shown by TLC to contain the desired product free of starting material and impurities.

"HPLC", herein, refers to high pressure liquid chromatography.

"Concentrating", as used herein, refers to concentration under reduced pressure, preferably at less than 50 mm. and at temperatures below 35° C.

"DIBAL", herein, refers to diisobutylaluminum hydride.

Preparation 1

11-Deoxy-10,11-didehydro-PGF$_{2\alpha}$, Methyl Ester and its 9$\beta$-epimer; and 11-Deoxy-10,11-didehydro-PGF$_{2\alpha}$ and its 9$\beta$-epimer.

A mixture of PGA$_2$, methyl ester (1.74 g.) and 12 ml. of tetrahydrofuran is treated at −78° C. with 24 ml. of 10% DIBAL in toluene. After one hour's stirring at −78° C., the mixture is quenched with 100 ml. of tetrahydrofuran-saturated aqueous ammonium chloride (1:1) and warmed to about 25° C. The mixture is acidified with sodium bisulfate and extracted with ethyl acetate. The organic phase is washed with sodium bisulfate, sodium carbonate, and brine, dried over sodium sulfate, and concentrated to yield 1.8 g.

The crude product is subjected to column chromatography to separate the title compounds, in the order:
11-deoxy-10,11-didehydro-PGF$_{2\alpha}$, methyl ester,
11-deoxy-10,11-didehydro-9$\beta$-PGF$_{2\alpha}$, methyl ester,
11-deoxy-10,11-didehydro-PGF$_{2\alpha}$, and
11-deoxy-10,11-didehydro-9$\beta$-PGF$_{2\alpha}$.

Preparation 2

2-Decarboxy-2-aminomethyl-PGF Compounds

The following description is provided from a commonly-owned, prior-filed U.S. Patent Application which will be incorporated by reference when that application matures in and issued patent.

Chart M shows the steps by which the formula CI, PGF$_{2\alpha}$- or 11-deoxy-PGF$_{2\alpha}$-type free acid is transformed to the various 2-decarboxy-2-aminomethyl or 2-decarboxy-2-(substituted amino)methyl-PGF$_\alpha$- or 11-deoxy-PGF$_\alpha$-type compounds of formulas CIV, CVI, CVII, CVIII, CIX, or CX.

In Chart M,
Y$_1$ is trans—CH=CH—; —C≡C—, or —CH$_2$CH$_2$—;
M$_1$ is

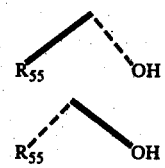

wherein R$_{55}$ is hydrogen or methyl;
L$_1$ is

CHART M

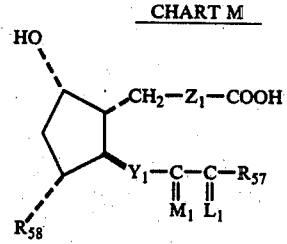

CI

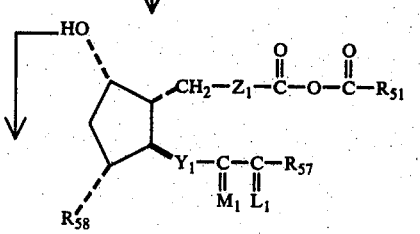

CII

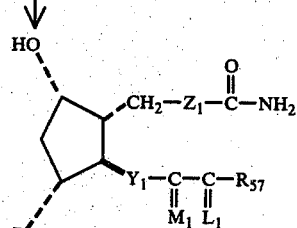

CIII

-continued
CHART M

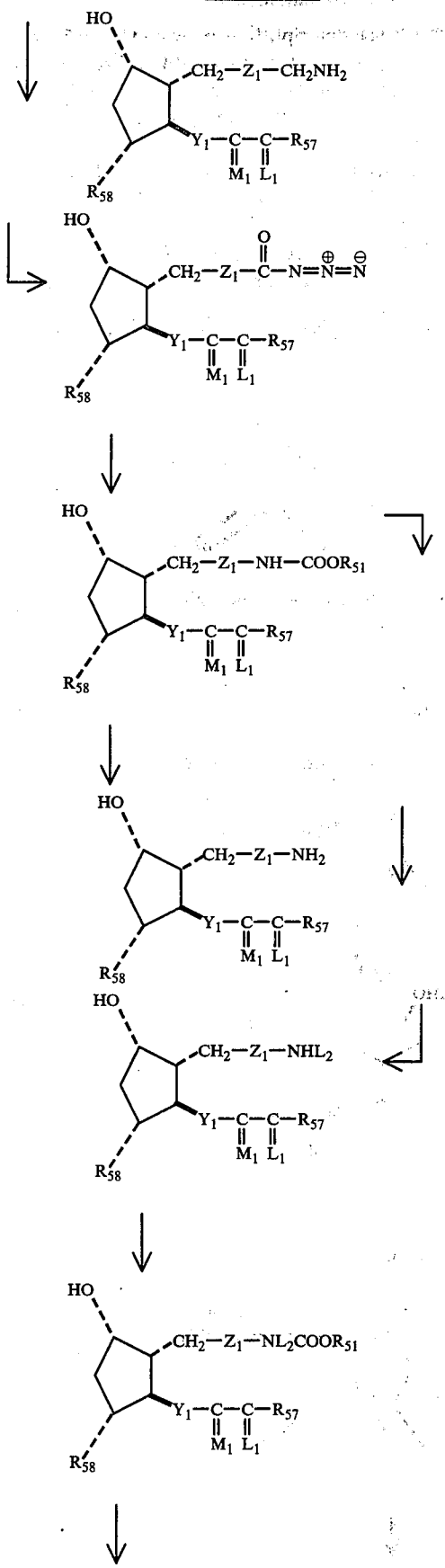

-continued
CHART M

CX
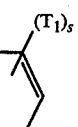

or a mixture of

and

wherein $R_{53}$ and $R_{54}$ are hydrogen, methyl, or fluoro, being the same or different, with the proviso that one of $R_{53}$ and $R_{54}$ is fluoro only when the other is hydrogen or fluoro;

$Z_1$ is
(1) cis—$CH=CH-CH_2-(CH_2)_w-CH_2-$,
(2) cis—$CH=CH-CH_2-(CH_2)_w-CF_2-$, wherein $w$ is one, 2, or 3;

$R_{57}$ is $-(CH_2)_m-CH_3$,  (1)

, or   (2)

,   (3)

wherein $m$ is one to 5, inclusive, $T_1$ is chloro, fluoro, trifluoromethyl, alkyl of one to 3 carbon atoms, inclusive, or alkoxy of one to 3 carbon atoms, inclusive, and $s$ is zero, one, 2, or 3, the various $T_1$'s being the same or different, with the proviso that not more than two $T_1$'s are other than alkyl, with the further proviso that $R_{57}$ is

, wherein $T_1$ and $s$ are as defined above, only when $R_{53}$ and $R_{54}$ are hydrogen or methyl, being the same or different;

$R_{58}$ is hydrogen or hydroxy;

$L_2$ and $L_3$ are hydrogen, alkyl of one to 4 carbon atoms, inclusive, or —$COOR_{51}$, wherein $R_{51}$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted one, 2, or 3 chloro or alkyl of one to 3 carbon atoms, inclusive; being the same or different, with the proviso that not more than one of $L_2$ and $L_3$ is —COOR$_{51}$.

By the procedure of Chart M the formula CI compound is transformed to a formula CII mixed acid anhydride. These mixed anhydrides are conveniently prepared from the corresponding alkyl, aralkyl, phenyl, or substituted phenyl chloroformate in the presence of an organic base (e.g., triethylamine). Reaction diluents include water in combination with water miscible organic solvents (e.g., tetrahydrofuran). This mixed anhydride is then transformed to either the formula CIII PG-type, amide or formula CV PG-type, azide.

For preparation of the PGF$_{2\alpha}$-type, amide (formula CIII) the formula CII mixed acid anhydride is reacted with liquid ammonia or ammonium hydroxide.

Alternatively, the formula CIII compound is prepared from the formula CI free acid by methods known in the art for transformation of carboxy acids to corresponding carboxyamides. For example, the free acid is transformed to a corresponding methyl ester (employing methods known in the art; e.g., excess etheral diazomethane), and a methyl ester thus prepared is transformed to the formula CIII amide.

Thereafter the formula CIV 2-decarboxy-2-aminomethyl-PGF$_{2\alpha}$- or 11-deoxy-PGF$_{2\alpha}$-type compound is prepared from the formula CIII compound by carbonyl reduction. Methods known in the art are employed in this transformation. For example, lithium aluminum hydride is conveniently employed.

The formula CII compound is alternatively used to prepare the formula CV azide. This reaction is conveniently carried out employing sodium azide by methods known in the art. See for example, Fieser and Fieser, Reagents for Organic Synthesis vol. 1, pgs. 1041–1043, wherein reagents and reaction conditions for the azide formation are discussed.

Finally, the formula CVI urethane is prepared from the formula CV azide reaction with an alkanol, aralkanol, phenol, or substituted phenol. For example, when methanol is employed the formula CVI compound is prepared wherein $R_1$ is methyl. This formula CVI PG-type product is then employed in the preparation of either the formula CVII or CVIII product.

In the preparation of the formula CVII primary amine from the formula CVI urethane, methods known in the art are employed. Thus, for example, treatment of the formula CVII urethane with strong base at temperatures above 50° C. are employed. For example, sodium, potassium, or lithium hydroxide is employed.

Alternatively, the formula CVI compound is employed in the preparation of the formula CVIII compound. Thus, when $L_2$ is alkyl the formula CVIII compound is prepared by reduction of the formula CVI urethane wherein $R_{51}$ is alkyl. For this purpose, lithium aluminum hydride is the conveniently employed reducing agent.

Thereafter, the formula CVIII product is used to prepare the corresponding CIX urethane by reaction of the formula CVIII secondary amine (wherein $L_2$ is alkyl) with an alkyl chloroformate. The reaction thus proceeds by methods known in the art for the preparation of carbamates from corresponding secondary amines. Finally, the formula CX product wherein $L_2$ and $L_3$ are both alkyl is prepared by reduction of the formula CIX carbamide. Accordingly, methods hereinabove described for the preparation of the formula CVIII compound from the formula CVI compound are used.

Preparation 1A

2-Decarboxy-2-azidomethyl-PGF$_{2\alpha}$.

(1) A solution of t-butyldimethylsilyl chloride (10 g.), imidazole (9.14 g.), and PGF$_{2\alpha}$ (3 g.) in 12 ml. of dimethylformamide are magnetically stirred under nitrogen atmosphere for 24 hr. The resulting mixture is then cooled in an ice bath and the reaction quenched by addition of ice water. The resulting mixture is then diluted with 150 ml. of water and extracted with diethyl ether. The combined ethereal extracts are then washed with water, saturated ammonium chloride, a sodium chloride solution, and thereafter dried over sodium sulfate. Solvent is removed under vacuum yielding PGF$_{2\alpha}$, t-butyldimethylsilyl ester, 9,11,15-tris-(t-butyldimethylsilyl)ether. NMR absorptions are observed at 0.20, 0.30, 0.83, 0.87, 0.89, 1.07–2.50, 3.10–4.21, and 5.38 $\delta$. Characteristic infrared absorptions are observed at 970, 1000, 1060, 1250, 1355, 1460, 1720, and 2950 cm.$^{-1}$.

(2) To a magnetically stirred suspension of lithium aluminum hydride (7.75 g.) in 18 ml. of diethyl ether is added dropwise at room temperature over a period of 12 min. 8.71 g. of the reaction product of part (1) above in 40 ml. of diethyl ether. After stirring at ambient temperature for one hr., the resulting product is cooled in an ice water bath and saturated sodium sulfate is added dropwise until the appearance of a milky suspension. The resulting product is coagulated with sodium sulfate, triturated with diethyl ether, and the solvent is removed by suction filtration. Concentration of the diethyl ether under vacuum yields 7.014 g. of 2-decarboxy-2-hydroxymethyl-PGF$_{2\alpha}$, 9,11,15-tris-(t-butyldimethylsilyl)ether. NMR absorptions are observed at 0.03, 0.82, 0.87, 1.10–2.60, 3.30–4.30, and 5.37 $\delta$. Characteristic infrared absorptions are observed at 775, 840, 970, 1065, 1250, 1460, 2895, 2995, and 3350 cm.$^{-1}$.

(3) p-Toluenesulfonyl chloride (3.514 g.), pyridine (44 ml.), and the reaction product of subpart (2), 7.014 g., are placed in a freezer at −20° C. for 3 days. Thereafter, 7.200 g. of 2-decarboxy-2-p-toluenesulfonyloxymethyl-PGF$_{2\alpha}$, 9,11,15-tris-(t-butyldimethylsilyl ether), is recovered, NMR absorptions are observed at 0.10, 0.94, 0.97, 1.10, 2.50, 4.03, 3.80–4.80, 5.45, 7.35, and 7.80 $\delta$. Infrared absorptions are observed at 775, 970, 1180, 1190, 1250, 1360, 1470, 2900, and 2995 cm.$^{-1}$. (4) The reaction product of subpart (3) (2.13 g.) is placed in 42 ml. of acetic acid, tetrahydrofuran, and water (3:1:1) containing 0.25 ml. of 10 percent aqueous hydrochloric acid. The reaction mixture becomes homogeneous after vigorous stirring for 16 hr. at room temperature. The resulting solution is then diluted with 500 ml. of ethyl acetate; washed with saturated sodium chloride and ethyl acetate; dried over sodium sulfate; and evaporated under reduced pressure, yielding 1.301 g. of an oil. Crude product is chromatographed on 150 g. of silica gel packed with ethyl acetate. Eluting with ethyl acetate yields 0.953 g. of 2-decarboxy-2-p-toluenesulfonyloxymethyl-PGF$_{2\alpha}$.

(5) The reaction product of subpart (4), (0.500 g.) in 5.0 ml. of dimethylformamide was added to a stirred suspension of sodium azide (1.5 g.) in 20 ml. of dimethylformamide. Stirring is continued at ambient temperature for 3 hr. The reaction mixture is then diluted with water (75 ml.), extracted with diethyl ether (500 ml.), and the etheral extracts washed successively with water, saturated sodium chloride, and dried over sodium sulfate. Removal of the diethyl ether under reduced pressure yields 0.364 g. of 2-decarboxy-2-azidomethyl-PGF$_{2\alpha}$. A characteristic azido infrared absorption is observed at 2110 cm.$^{-1}$.

Preparation 1B

2-Decarboxy-2-aminomethyl-PGF$_{2\alpha}$

Crude decarboxy-2-azidomethyl-PGF$_{2\alpha}$ (Prep. 1A, 0.364 g.) in 12 ml. of diethyl ether is added to a magnetically stirred suspension of lithium aluminum hydride (0.380 g.) in 20 ml. of diethyl ether. Reaction temperature is maintained at about 0° C. and addition of lithium aluminum hydride proceeds dropwise over a 4 min. period. After addition is complete, the resulting mixture is stirred at ambient temperature for 1.5 hr. and thereafter placed in an ice bath (0°–5° C.). Excess reducing agent is then destroyed by addition of saturated sodium sulfate. After cessation of gas evolution, the resulting product is coagulated with sodium sulfate, triturated with diethyl ether, and solid salts removed by filtration. The filtrate is then dried with sodium sulfate, and evaporated under reduced pressure to yield 0.304 g. of a slightly yellow oil. This oil (100 mg.) is then purified by preparative thin layer chromatography, yielding 42 g. of title product. NMR absorptions are observed at 0.90, 1.10–2.80, 3.28, 3.65–4.25, and 5.45 δ. Characteristic infrared absorptions are observed at 970, 1060, 1460, 2995, and 3400 cm.$^{-1}$. The mass spectrum shows parent peak at 699.4786 and other peaks at 628, 684, 595, 217, and 274.

Preparation 3

13,14-Dihydro-(15RS)-PGF$_{2\alpha}$, Methyl Ester.

This compound was reported by Hambert et al., Ann. N.Y. Acad. Sci. 180, 164 (1971). An alternate preparation is as follows.

A. A mixture of 2-hydroxy-4-benzoxy-5-(1'-trans-3'-oxo-octenyl)cyclopentanyl acetic acid γ-lactone (U.S. Pat. No. 3,778,450, 0.370 g.), 20 ml. of 95% ethanol, and 100 mg. of 10% palladium-on-carbon catalyst is hydrogenated at about 25° C. at one atmosphere. After 20 min. the mixture is filtered and concentrated.

B. The above residue is reduced with sodium borohydride (0.200 g.) in 10 ml. of methanol at 0° C. for 10 min. Then acetic acid and water are added, the mixture concentrated somewhat and then diluted with ethyl acetate. The organic phase is washed with aqueous sodium bicarbonate, and brine, dried, and concentrated. The residue is chromatographed on silica gel, eluting with ethyl acetate to yield the (3'RS)-hydroxy lactone, 0.262 g., having R$_f$ 0.52 (TLC on silica gel in ethyl acetate-hexane (1:1)).

The above hydrogenation and reduction on a 10-fold scale, yields 3.36 g.

C. The product of part B (3.62 g. total is dissolved in 45 ml. of methanol and treated with potassium carbonate (1.4 g.) at about 25° C. for 2 hrs. Then 5 ml. of water is added, the mixture is concentrated to remove methanol, 3N hydrochloric acid is added to pH 1, and sodium chloride is added to saturation. The mixture is extracted with ethyl acetate and the organic phase is washed with brine, dried over sodium sulfate, and concentrated to an oil, 3.036 g. The product is completely lactonized by heating in 20 ml. toluene at reflux.

D. The lactone of part C above, in 50 ml. of methylene dichloride, is converted to the di-THP ether by treating with 18 ml. of dihydropyran at about 15°–25° C. in the presence of 15 mg. of p-toluenesulfonic acid for 10 min. Then 20 ml. of saturated aqueous sodium bicarbonate is added and the organic phase is washed with brine, dried over sodium sulfate, and concentrated. The residue is chromatographed on silica gel, eluting with ethyl acetate (60%)-Skellysolve B to yield 3.27 g., now 2-hydroxy-4-tetrahydropyran-2-yloxy-5-[3'-(tetrahyropyran-2-yloxy)-octyl]cyclopentanyl acetic acid γ-lactone.

E. The lactone of part D is reduced to the corresponding lactol. The lactone (3.270 g.) in 89 ml. of toluene is treated at −60° to −70° C. with 25 ml. of dibutylaluminum hydride (10% in toluene) added over 30 min. and stirred for 2 hours. The reaction is quenched with 5 ml. water in 9 ml. of tetrahydrofuran added cautiously and stirred for 30 min. Solids are removed and the organic phase is washed with brine, dried, and concentrated to the lactol, 3.261 g.

F. The carboxyl side chain is added by the Wittig reaction. To a freshly prepared sodium methylsulfinylmethide reagent (Fieser et al., Reagents for Organic Syntheses, Wiley, 1967) prepared from 18 ml. of dimethylsulfoxide and sodium hydride (1.25 g. 50%) heated cautiously at 55°–60° and then at 65°–70° and then cooled to 15° C. is added a solution of 4-carboxybutyltriphenylphosphonium bromide (6.33 g.) in 8.9 ml. of dimethylsulfoxide, with stirring for 15 min. Then a solution of the lactol of part E (3.261 g.) in 5.34 ml. of dimethylsulfoxide and 7.1 ml. of benzene is added over a 15 min. period. Stirring at 25° C. is continued for one hour and then the mixture is poured into ice-benzene, acidified to pH 2 with 1 N potassium hydrogen sulfate, and separated. The organic phase is washed with brine, dried over sodium sulfate, and concentrated. The residue is chromatographed on silica gel, pretreated with ethyl acetate-Skellysolve B-acetic acid (20:78:2), eluting with ethyl acetate (25–75%)-Skellysolve B to yield 13,14-dihydro-(15RS)-PGF$_{2\alpha}$, 11,15-bis(tetrahydropyran-2-yl)ether, 0.721 g. having R$_f$ 0.04 (TLC on silica gel in ethyl acetate-Skellysolve B (1:1)).

G. The product of part F is methylated with diazomethane in the conventional manner and is then hydrolyzed to remove blocking groups in acetic-acid-tetrahydrofuran-water (13.8:2.35:6.9 ml.) at 40° C. for 4 hours. The mixture is concentrated, diluted with water, and freeze-dried. The residue is chromatographed on silica gel, eluting with ethyl acetate-(75–100%)-Skellysolve B, to yield the title compound, 0.250 g., having NMR peaks at 5.2–5.6, 4.03, 3.87, 3.67 and 3.2 δ.

EXAMPLE 1

5ξ-Iodo-9-deoxy-6ξ,9α-epoxymethano-PGF$_1$, Amide, less polar and more polar isomers (Formula XVIII: L is —(CH$_2$)$_3$—, Q is

R$_4$ is n-pentyl, R$_9$ and R$_{18}$ are hydrogen, R$_{19}$ is iodo, R$_{20}$ is

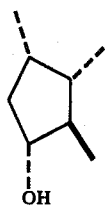

and X is trans—CH=CH—).

Refer to Chart B. A solution of the formula-III or XVII iodo-ether acid, mixed isomers (Example 13, 1.0 g.) in 10 ml. of acetone is cooled to about −10° C. and treated with 0.6 ml. of triethylamine and 0.6 ml. of isobutyl chloroformate. After 5 min. there is added 20 ml. of acetonitrile saturated with ammonia, and the reaction mixture allowed to warm to about 25° C. The mixture is filtered, and the filtrate concentrated. The residue is taken up in ethyl acetate and water. The organic phase is washed with water, dried over magnesium sulfate and concentrated. The residue is subjected to silica gel chromatography, eluting with acetone (25–100%)-methylene chloride. There are obtained the formula-XVIII iodo-ether, amide, less polar isomer; a fraction of mixed less and more polar isomers; and the more polar isomer.

EXAMPLE 2

5ξ-Iodo-9-deoxy-6ξ,9α-epoxymethano-PGF$_1$, Methylamide, mixed isomers (Formula XVIII: R$_9$ is hydrogen and R$_{18}$ is methyl).

Refer to Chart B. A solution of the formula-III or XVII 5ξ-iodo-9-deoxy-6ξ,9α-epoxymethano-PGF$_1$, mixed isomers (Example 13, 1.0 g.) in 10 ml. of acetone is treated with 0.3 ml. of triethylamine and cooled to −5° C. Thereupon 0.26 ml. of isobutyl chloroform is added, with stirring at 0° C. for 5 min., followed by 5 ml. of 3M methylamine in acetonitrile. The solution is stirred for 20 min. more as it warmed to about 25° C. The mixture is filtered and concentrated. The oily residue is triturated with methylene chloride, and filtered to remove a precipitate. The filtrate is subjected to silica gel chromatography, eluting with acetone (50–90%)-methylene chloride, to yield the 5ξ-iodo-9-deoxy-6ξ,9α-epoxymethano-PGF$_1$, methylamide mixed isomers.

EXAMPLE 3

5ξ-Iodo-6ξ,9α-epoxymethano-PGF$_1$, n-Butylamide, Mixed Isomers (Formula: XVIII: R$_9$ is hydrogen and R$_{18}$ is n-butyl).

Refer to Chart B. A solution of the formula-III or XVII iodo-ether acid, mixed isomers (Example 13, 1.0 g.) in 10 ml. of acetone is cooled to about −10° C. and treated with 2.0 ml. of triethylamine and 0.38 ml. of isobutyl chloroformate. After 6 min. there is added a solution of 3 ml. of n-butylamine in 4 ml. of acetone. After about 15 min. the reaction mixture is allowed to warm to about 25° C. and stirred for 3 hr. The mixture is concentrated and the residue is taken up in ethyl acetate. The solution is washed with water and brine, dried over magnesium sulfate, and concentrated. The residue is chromatographed on silica gel, eluting with acetone (5–100%)-methylene chloride to yield the title compound. The product is rechromatographed to remove color using silica gel and eluting with acetone-methylene chloride (1:3).

EXAMPLE 4

5ξ-Iodo-9-deoxy-6ξ,9α-epoxymethano-PGF$_1$, Benzylamide, mixed isomers (Formula XVIII: R$_9$ is hydrogen and R$_{18}$ is benzyl).

Refer to Chart B. Following the procedures of Example 1, there are used 1.0 g. of the formula-III or XVII 5ξ-iodo-9-deoxy-6ξ,9α-epoxymethano-PFG$_1$, mixed isomers, and 0.22 g. of benzylamine instead of methylamine. The crude product is chromatographed on silica gel, eluting with acetone (50–70%)-methylene chloride, to yield the 5ξ-iodo-9-deoxy-6ξ-9α-epoxymethano-PGF$_1$, benzylamide mixed isomers.

EXAMPLE 5

5ξ-Iodo-9-deoxy-6ξ,9α-epoxymethano-PFG$_1$, Anilide, mixed isomers (Formula XVIII: R$_9$ is hydrogen, R$_{18}$ is phenyl).

Refer to Chart B. Following the procedure of Example 1, there are used 1.0 g. of the formula-III or XVII 5ξ-iodo-9-deoxy-6ξ,9α-epoxymethano-PFG$_1$, mixed isomers, and 0.1 g. of aniline. The crude product is chromatographed on silica gel, eluting with acetone (10–50%)-methylene chloride, to yield the 5ξ-iodo-9-deoxy-6ξ,9α-epoxymethano-PGF$_1$, anilide mixed isomers.

EXAMPLE 6

5ξ-Iodo-9-deoxy-6ξ,9α-epoxymethano-17-phenyl-18,19,20-trinor-PGF$_1$, Methyl Ester mixed isomers (Formula III: L is —(CH$_2$)$_3$—, Q$_1$ is

R$_1$ is —COOCH$_3$, R$_4$ is

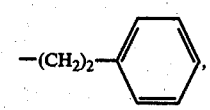

R$_{19}$ is iodo, (R$_{21}$) is

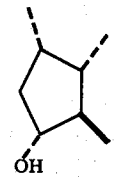

and X is trans —CH=CH—).

Refer to Chart A. A solution of 9-deoxy-9α-hydroxymethyl-17-phenyl-18,19,20-trinor-PFG$_{1\alpha}$, methyl ester (1.0 g.) in 25 ml. of dichloromethane, cooled in an ice bath, is treated with anhydrous sodium carbonate (0.45 g.) and iodine (0.55 g.) and stirred for one hr. Thereafter the mixture is allowed to warm to 25° C., with stirring for 16 hr. The reaction mixture is diluted with 50 ml. of dichloromethane and treated with 20 ml. of 10% aqueous sodium sulfite. After the iodine color has disappeared, the organic phase, together with organic extractions of the aqueous phase with dichloromethane, is dried and concentrated to a pale yellow oil. The oil is subjected to silica gel chromatography to yield the formula-III 9-deoxy-6ξ,9α-epoxymethano-5-iodo-17- phenyl-18,19,20-trinor-PGF₁, methyl ester, mixed isomers.

EXAMPLE 7

5ξ-Bromo-9-deoxy-6ξ,9α-epoxymethano-PGF₁, Methyl Ester, mixed isomers (Formula III: L is —(CH₂)₃—, Q₁ is

R₁ is —COOCH₃, R₄ is n-pentyl, R₁₉ is bromo, (R₂₁) is

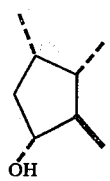

and X is trans—CH=CH—).

Refer to Chart A. A solution of 9-deoxy-9α-hydroxymethyl-PGF₂α, methyl ester (1.00 g.) in 25 ml. of methylene chloride is treated at about 0° C. with N-bromosuccinimide (0.50 g.) added in portions within 3 min. After additional stirring for 10 min. the reaction is complete as shown by TLC (on silica gel in ethyl acetate). The solution is washed with aqueous sodium sulfite and water, dried over magnesium sulfate, and concentrated. The colorless oily residue is chromatographed on silica gel, eluting with acetone (20–40%)-methylene chloride to yield the mixed isomers of the formula-III 5-bromo title compound.

EXAMPLE 8

(5R,6R)-5-Iodo-9-deoxy-6,9α-epoxymethano-PFG₁, Methyl Ester and (5S,6S)-5-Iodo-5-Iodo-9-deoxy-6,9α-epoxy-PFG₁, Methyl Ester.

Refer to Chart A. A suspension of 9-deoxy-9α-hydroxymethyl-PGF₂α, methyl ester (3.0 g.) in 60 ml. of water is treated with sodium carbonate (1.7 g.) and cooled in an ice bath. To the resulting solution is added potassium iodide (2.7 g.) and iodide (4.14 g.) and stirring continued for 3 hr. at about 0° C. Thereafter sodium sulfite (2.5 g.) and sodium carbonate (0.8 g.) are added to decolorize the mixture. After a few minutes the mixture is extracted with chloroform. The organic phase is washed with brine, dried over sodium sulfate, and concentrated to yield mainly the title compound, an oil, which is further purified by silica gel chromatography, eluting with methylene chloride (15–50%)-acetone to yield the less polar title compound and the more polar title compound.

EXAMPLE 9

5ξ-Iodo-9-deoxy-6ξ,9α-epoxymethano-PGF₁, Methyl Ester, less polar isomer and more polar isomer (Formula III)

Refer to Chart A. A solution of formula-IX 9-deoxy-9-hydroxymethyl-PGF₂α, 11,15-bis(triphenylsilyl ether), methyl ester (U.S. Pat. No. 3,950,363, 1.71 g.) in 14 ml. of methylene dichloride and 14 ml. of water is cooled in an ice bath and treated successively with sodium carbonate (208 mg.), potassium iodide (623 mg.), and iodine (952 mg.) and then stirred for 4 hr. The mixture is decolorized with 10% aqueous sodium sulfite and then diluted with methylene chloride and water. The aqueous phase is separated, extracted with ethyl acetate, and the organic phases are combined. The organic phase is washed with brine, dried over magnesium sulfate, and concentrated. The residue (2.092 g.) is chromatographed on silica gel, eluting with ethyl acetate (60–100%)-hexane to yield three fractions (1) 1.712 g., incompletely desilylated, (2) less polar title compound 0.092 g., and (3) more polar title compound, 0.028 g.

Fraction (1) is treated with tetrahydrofuran-water-85%-phosphoric acid (80 ml.:60 ml.:2 ml.) at 40° C. for 5.5 hrs. and at about 25° C. for 16 hr. The mixture is concentrated somewhat, then mixed with ethyl acetate-5% aqueous sodium bicarbonate and separated. The organic phase is washed with brine, dried, and concentrated. The residue is chromatographed on silica gel, eluting with ethyl acetate to yield three fractions: (a) 1.24 g., (b) less polar title compound, 0.221 g., and (c) more polar title compound, 0.057 g.

The less polar title compound has $R_f$ 0.55 (TLC on silica gel in ethyl acetate), infrared absorption at 3300 and 1735 cm$^{-1}$, NMR peaks at 5.3–5.7, 3.6, and 2.8–4.2, and mass spectral lines (TMS) at 652.2454, 637, 621, 581, 562, 525, 524, 491, 465, and 173. The more polar title compound has $R_f$ 0.45 (TLC on silica gel in ethyl acetate), and other spectral data essentially the same as for the less polar isomer. The high resolution mass spectral peak is at 637.2224.

EXAMPLE 10

9-Deoxy-6ξ,9α-epoxymethano-Δ⁵-PGF₁, Methyl Ester (Formula IV)

Refer to Chart C. A solution of Formula-III 5ξ-iodo-9-deoxy-6ξ,9α-epoxymethano-PGF₁, methyl ester (Example 9, 95 mg.) in 3 ml. of benzene is treated with 0.24 ml. of DBU and heated at 40° C. for 24 hrs. The mixture is filtered to remove a precipitate, and the filtrate is washed with brine and water, dried over sodium sulfate, and concentrated. The residue is the title compound, 71 mg., having $R_f$ 0.30 (TLC on silica gel in ethyl acetate), infrared absorption at 3400 and 1750 cm$^{-1}$, NMR peaks at 5.4–5.7, 3.65, 3.5–4.3, and 3.0–3.3 δ, and mass spectral lines (TMS) at 524.3365, 509, 495, 453, 434, 403, 363, 351, 344, 238, and 173.

EXAMPLE 11

5ξ-Iodo-9-deoxy-6ξ,9α-epoxymethano-PGF₁, Methyl Ester Mixed Isomers and Separated Isomers (Formula III: L is —(CH₂)₃—, Q₁ is

R₁ is —COOCH₃, R₄ is n-pentyl, R₁₉ is iodo, (R₂₁) is

and X is trans—CH=CH—).

Refer to Chart A, step "a". A suspension of the formula-IX 9-deoxy-9α-hydroxymethyl-PGF₂α, methyl ester as its 11,15-bis(tetrahydropyranyl) ether (2.0 g.) in 23 ml. of water is treated with sodium bicarbonate (0.7 g.) and cooled in an ice bath. To the resulting solution is added potassium iodide (1.93 g.) and iodine (2.82 g.) and stirring continued for 16 hr. at about 0° C. Thereafter a solution of sodium sulfite (1.66 g.) and sodium carbonate (0.76 g.) in 10 ml. of water is added. After a few minutes the mixture is extracted with chloroform. The organic phase is washed with brine, dried over sodium sulfate, and concentrated to yield mainly the bis(tetrahydropyranyl) ether of the title compound. Hydrolysis of this ether in acetic acid-water-tetrahydrofuran (20:10:3) yields mainly the title compound, which is further purified by silica gel chromatography.

Following the procedures of Example 11, as illustrated in Chart A, but replacing the formula-IX starting material with the following formula-IX compounds or C-11 derivatives within the scope of formula-IX:
9-Deoxy-9α-hydroxymethyl-15-methyl-$PGF_{2α}$
9-Deoxy-9α-hydroxymethyl-15-ethyl-$PGF_{2α}$
9-Deoxy-9α-hydroxymethyl-16,16-dimethyl-$PGF_{2α}$
9-Deoxy-9α-hydroxymethyl-16,16-difluoro-$PGF_{2α}$
9-Deoxy-9α-hydroxymethyl-16-phenoxy-17,18,19,20-tetranor-$PGF_{2α}$
9-Deoxy-9α-hydroxymethyl-11-deoxy-11-oxo-$PGF_{2α}$
9-Deoxy-9α-hydroxymethyl-11-deoxy-$PGF_{2α}$
9-Deoxy-9α-hydroxymethyl-2a,2b-dihomo-$PGF_{2α}$
9-Deoxy-9α-hydroxymethyl-3-oxa-$PGF_{2α}$
9-Deoxy-9α-hydroxymethyl-3-oxa-17-phenyl-18,19,20-trinor-$PGF_{2α}$
there are obtained the corresponding formula-III iodo compounds. Those iodo compounds obtained from non-blocked formula-IX compounds are identified by formula XII in Chart C herein.

EXAMPLE 12

9-Deoxy-9α-hydroxymethyl-6-keto-$PGF_{1α}$, Methyl Ester (Formula I: L, $R_1$, $R_4$, and X as defined in Example 11, Q is and $(R_{20})$ is

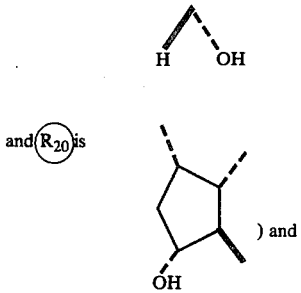

) and

9-Deoxy-6ξ,9α-epoxy methano-6ξ-hydroxy-$PGF_1$, Methyl Ester (Formula II).

Refer to Chart A, step "b". A solution of the formula-III iodo compound, methyl ester (Example 1, 0.45 g.) in 20 ml. of tetrahydrofuran is treated with silver carbonate (0.250 g.) and perchloric acid (90%, 0.10 ml.), and stirred at about 25° C. for 24 hr. The mixture is diluted with 25 ml. of ethyl acetate and the organic phase is washed with saturated sodium carbonate solution and brine, dried, and concentrated to an oil. Separation by silica gel chromatography eluting with ethyl acetate-Skellysolve B yields mainly the formula-I title compound as a more polar material than the formula-III starting material, as well as a minor amount of the formula-II compound.

Following the procedures of Example 12, but replacing the formula-III iodo compound therein with those formula-III iodo compounds described subsequent to Example 11, there are obtained the corresponding formula-I and -II keto and hydroxy compounds.

EXAMPLE 13

5ξ-Iodo-9-deoxy-6ξ,9α-epoxymethano-$PGF_1$, Mixed Isomers (Formula III) and 9-Deoxy-6ξ,9α-epoxymethano-6ξ-hydroxy-$PGF_1$ (Formula II) and 9-Deoxy-9α-hydroxymethyl-6-keto-$PGF_{1α}$ (Formula I).

Refer to Chart A. A solution of the formula-III iodo compound methyl ester (Example 11, 1.0 g.) in 30 ml. of methanol is treated with 20 ml. of 3N aqueous potassium hydroxide at about 0° C. for about 5 min., then at about 25° C. for 2 hr. The mixture is acidified with 45 ml. of 2N potassium acid sulfate and 50 ml. of water to pH 1.0, saturated with sodium chloride and extracted with ethyl acetate. The organic phase is washed with brine, dried over sodium sulfate and concentrated to an oil. The oil is subjected to silica gel chromatography, eluting with acetone-dichloromethane to yield, first the formula-III free acid compound and later, the mixed formula-I and -II compounds as a more polar fraction.

EXAMPLE 14

9-Deoxy-9α-hydroxymethyl-6-keto-$PGF_{1α}$ (Formula I) and 9-Deoxy-6ξ,9α-epoxymethano-6ξ-hydroxy-$PGF_1$ (Formula II).

Refer to Chart A. A solution of 9-deoxy-9α-hydroxymethyl-6-keto-$PGF_{1α}$, methyl ester (Example 12, 0.52 g.) in 20 ml. of methanol, cooled in an ice bath, is treated with 10 ml. of 1 N aqueous potassium hydroxide. After 10 minutes the mixture is warmed to about 25° C. and stirring continued for 2 hours longer. The mixture is acidified with aqueous potassium hydrogen sulfate, with cooling, and then extracted with ethyl acetate. The extract is washed with brine, dried over magnesium sulfate, and concentrated to the title compounds.

EXAMPLE 15

(5Z)-9-Deoxy-6,9α-epoxymethano-Δ$^5$-$PGF_1$, Methyl Ester (Formula IV: L is —($CH_2$)$_3$—, Q is

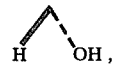

$R_1$ is —$COOCH_3$, $R_4$ is n-pentyl, $(R_{20})$ is

and X is trans—CH═CH—).

Refer to Chart C. A mixture of the formula-XIII iodo compound 5ξ-iodo-9-deoxy-6ξ,9α-epoxymethano-$PGF_1$, methyl ester (Example 11, 0.25 g.) 0.25 ml. of 1,5-diazabicyclo-[4.3.0]nonene-5 (DBN), and 15 ml. of benzene is left standing at about 25° C. for 72 hr. and then warmed to 45° C. for 4 hr. The resulting mixture is cooled, mixed with ice water and a small amount of diethyl ether, and the layers separated. The organic phase is dried over magnesium sulfate and concentrated to the title compound.

Following the procedures of the above Example 7 but replacing DBN with DBU, using 0.75 ml. DBU with 0.5 g. iodo compound, there is obtained 0.44 g. product.

Following the procedures of Example 15, but replacing the formula-XII iodo compound with those formula-XII iodo compounds described subsequent to Example 11, there are obtained the corresponding formula-IV enol ethers.

EXAMPLE 16

(5Z)-9-Deoxy-6,9α-epoxymethano-$\Delta^5$-PGF$_1$, Methyl Ester (Formula IV).

Refer to Chart C. A mixture of the formula-XII 9-deoxy-6,9-epoxymethano-5-iodo-PGF$_{1\alpha}$, methyl ester (Example 11, 0.213 g.) in 3 ml. of dimethylformamide is treated with a fresh solution of potassium superoxide (0.45 g.) in 10 ml. of dimethylformamide containing dicyclohexyl-18-crown-6 (0.75 g.) in an ice bath. After about 20 min. the reaction mixture is quenched in ice water, thereafter extracted with diethyl ether. The organic phase is dried over magnesium sulfate and concentrated to yield the title compound, having the properties as the product of Example 15.

The above product is subjected to column chromatography on Florisil ® pretreated with triethylamine (5%)-dichloromethane. The product is eluted with ethyl acetate-hexanetriethylamine to give the title compound.

Following the procedure of Example 16, but replacing potassium superoxide with each of the following reagents, the title compound is likewise obtained:
sodium superoxide
tetramethylammonium superoxide
sodium carbonate
potassium carbonate
sodium hydroxide
potassium hydroxide
sodium benzoate
potassium benzoate
sodium acetate
potassium acetate
sodium trifluoroacetate
potassium trifluoroacetate
sodium bicarbonate
potassium bicarbonate and
silver acetate

EXAMPLE 17

(5Z)-9-Deoxy-6,9α-epoxymethano-$\Delta^5$-PGF$_1$, 11,15-diacetate, Methyl Ester I. A mixture of (5Z)-9-deoxy-6,9α-epoxymethano-$\Delta^5$-PGF$_1$, methyl ester (Example 15, estd. 1.35 g., derived from 1.6 g. of 5-iodo intermediate) in 7.5 ml. of pyridine is treated with 2.5 ml. of acetic anhydride at about 25° C. for 2.25 hr. Then ice and ethyl acetate are added and the organic phase is washed with water and brine, dried over sodium sulfate, and concentrated. The residue is chromatographed on Florisil ® which is pretreated with triethylamine (5%)-Skellysolve B eluting with ethyl acetate (5-50%)-Skellysolve B-triethylamine (0.1%) to yield the title compound.

II. Alternatively, the 5-iodo intermediate is acetylated prior to dehydrohalogenation. A mixture of 5ξ-iodo-9-deoxy-6ξ,9α-epoxymethano-PGF$_1$, methyl ester (1.0 g.) in 7.5 ml. of pyridine is treated with 2.5 ml. of acetic anhydride at about 25° C. for one hour, then at 40°-50° C. for 1.5 hrs. The mixture is diluted with ice and ethyl acetate and the organic phase is washed with water and brine, dried over sodium sulfate and concentrated. The residue is treated with 2 ml. of DBU at about 25° C. for 3 days. The mixture is washed with water and brine, and the organic phase is dried and concentrated to the title compound.

The title compound is transformed to (5Z)-9-deoxy-6,9α-epoxymethano-$\Delta^5$-PGF$_1$, sodium salt, by treating with a mole equivalent of sodium methoxide in methanol at about 25° C. for 4.25 hr. The mixture is concentrated, then taken up in methanol-water (5:1) and stirred 16 hr. The mixture is freeze-dried to produce the solid sodium salt.

EXAMPLE 18

9-Deoxy-9α-hydroxymethyl-6-keto-PGF$_{1\alpha}$, 11,15-diacetate, Methyl Ester

A solution of (5Z)-9-deoxy-6,9α-epoxymethano-$\Delta^5$-PGF$_1$, 11,15-diacetate, methyl ester (Example 17, estd. 4.29 g.) in 100 ml. of tetrahydrofuran is diluted with 34 ml. of water and treated with 10.3 ml. of acetic acid, with stirring, at about 25° C. for 2.5 hr. The mixture is diluted with ethyl acetate and the organic phase is washed with aqueous sodium bicarbonate and brine, dried over sodium sulfate, and concentrated. The residue is chromatographed on silica gel, eluting with ethyl acetate-Skellysolve B, to yield the title compound.

EXAMPLE 19

(5Z)-9-Deoxy-6,9α-epoxymethano-$\Delta^5$-PGF$_1$, Methyl Ester, 11,15-bis(Tetrahydropyran-2-yl)ether.

A mixture of 5 -iodo-9-deoxy-6 ,9α-epoxymethano-PGF$_{1\alpha}$, 11,15-bis(tetrahydropyran-2-yl)ether, methyl ester (Example 11, 3.0 g.) in 100 ml. of benzene is treated with 4 ml. DBN at 40° C. for 4 hrs., then left at about 25° C. for 64 hrs. The mixture is washed with ice-water, dried over magnesium sulfate, and concentrated to the title compound.

EXAMPLE 20

5ξ-Iodo-9-deoxy-6ξ,9α-epoxymethano-PGF$_1$, p-Phenylphenacyl Ester (Formula XIII) and (5Z)-9-Deoxy-6,9α-epoxymethano-$\Delta^5$-PGF$_1$, p-Phenylphenacyl Ester (Formula IV).

A. Refer to Chart C. A mixture of the formula-XIII iodo acid compound (Example 13, 0.20 g.), p-phenylphenacyl bromide (0.50 g.), 0.4 ml. of diisopropylethylamine, and 10 ml. of acetonitrile is stirred at about 25° C. for 40 min. It is mixed with dilute aqueous citric acid and brine and extracted with ethyl acetate. The organic phase is dried and concentrated. The residue is subjected to silica gel chromatography, eluting with ethyl acetate-Skellysolve B to yield the title 5-iodo compound.

B. The product of Part A above (0.20 g.) is treated with 0.4 ml. of DBN in 15 ml. of benzene at 42° C. for 22 hr. The reaction mixture is cooled, washed with ice-water containing sodium chloride, dried over magnesium sulfate and and concentrated to the second title compound. The residue is subjected to chromatographic separation on a Florisil ® column pretreated with hexane-ethyl acetatetriethylamine, eluting with ethyl acetate to yield the formula-IV compound.

EXAMPLE 21

(5Z)-9-Deoxy-6,9α-epoxymethano-$\Delta^5$-PGF$_1$, Sodium Salt.

A mixture of (5Z)-9-deoxy-6,9α-epoxymethano-Δ$^5$-PGF$_1$, methyl ester (Example 15, 0.030 g.) in 5 ml. of methanol is treated with 9 ml. of 0.01 N. NaOH and stirred at about 25° C. for 72 hr. The solution is then diluted with 5 ml. of water, frozen at about −75° C. and lyophilized overnight. The title compound is obtained as a white free-flowing powder.

Following the procedure of Example 21 but replacing sodium hydroxide with excess sodium carbonate suspended in water, there is obtained the title compound after 72 hr. at about 25° C.

EXAMPLE 22

9-Deoxy-9α-hydroxymethyl-6-keto-11β-PGF$_{1α}$, Methyl Ester (Formula I: L is —(CH$_2$)$_3$—, Q is

R$_1$ is —COOCH$_3$, R$_4$ is n-pentyl,  is and X is trans—CH=CH—).

Refer to Chart A. There is first prepared 5ξ-iodo-9-deoxy-6ξ,9α-epoxymethano-11β-PGF$_1$, methyl ester. A solution of 9-deoxy-9α-hydroxymethyl-11β-PGF$_{2α}$, methyl ester (1.0 g.) in 15 ml. of chloroform is treated at −10° C. with anhydrous sodium carbonate (0.29 g.) and iodine (0.35 g.). The mixture is stirred for 30 min., then washed with sodium sulfite solution and brine, dried, and concentrated. The residue is chromatographed on silica gel (eluting with acetone-methylene chloride to yield a mixture of the isomers of the 5-iodo compound.

The above 5-iodo compound (0.71 g.) is treated in 20 ml. of tetrahydrofuran with silver carbonate (0.35 g.) and about 0.1 ml. of 70% perchloric acid at about 25° C. in the dark for 20 hr. The mixture is filtered, the cake is washed with ethyl acetate, and the combined filtrates are concentrated to about one-third volume. The concentrate is diluted with water and extracted with ethyl acetate. The extract is washed, dried, and concentrated, to the title compound.

EXAMPLE 23

9-Deoxy-9α-hydroxymethyl-6-keto-11β-PGF$_{1α}$ (Formula-I: L, Q, R$_4$, R$_{20}$ and X as defined in Example 22, and R$_1$ is —COOH).

A solution of 9-deoxy-9α-hydroxymethyl-6-keto-11β-PGF$_{1α}$, methyl ester (Example 22, 0.35 g.) in 20 ml. of methanol is treated with 5 ml. of 1N aqueous potassium hydroxide for 2.5 hr. The mixture is acidified with potassium hydrogen sulfate solution, diluted with brine, and extracted with ethyl acetate. The extract is washed with brine, dried, and concentrated to an oil. The oil is chromatographed on silica gel, eluting with acetone-methylene chloride to yield the title compound. The corresponding 9-deoxy-6 ,9α-epoxymethano-6 -hydroxy-11β-PGF$_1$ compound is also present in the equilibrium mixture.

EXAMPLE 24

(5Z)-9-Deoxy-6,9α-epoxymethano-Δ$^5$-11-deoxy-PGF$_1$, Methyl Ester (Formula IV: L is —(CH$_2$)$_3$—, Q is

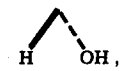

R$_1$ is —COOCH$_3$, R$_4$ is n-pentyl, 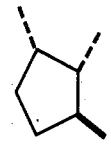 is and X is trans—CH=CH—).

Refer to Chart C. There is first prepared the formula-XIII 5-bromo intermediate. A solution of 9-deoxy-9α-hydroxymethyl-11-deoxy-PGF$_{2α}$, methyl ester (0.600 g.) in 26 ml. of methylene chloride is treated at 0° C. with N-bromosuccinimide (0.348 g.) for 20 min. Then a solution of sodium sulfite (0.255 g. in 9 ml. of water) is added, and the organic phase is washed with water and brine, dried and concentrated. The residue is chromatographed on silica gel, eluting with ethyl acetate-Skellysolve B to yield the 5ξ-bromo-9,11-dideoxy-6ξ,9α-epoxymethano-PGF$_1$, methyl ester, 0.620 g.

The above 5-bromo intermediate is treated in benzene (30 ml.) with 1.25 ml. of DBU at reflux for 24 hr. The mixture is washed with ice-water, then with water and brine, dried and concentrated. The residue is chromatographed on silica gel pretreated with ethyl acetate-Skellysolve B-triethylamine, eluting with ethyl acetate-Skellysolve B-triethylamine, to yield the title compound.

EXAMPLE 25

9,11-Dideoxy-9α-hydroxymethyl-6-keto-PGF$_{1α}$, Methyl Ester (Formula I).

A solution of (5Z)-9,11-dideoxy-6,9α-epoxymethano-PGF$_1$, methyl ester (Example 24, 0.543 g.) in 8 ml. of tetrahydrofuran, 2 ml. of water, and 1 ml. of acetic acid is stirred at about 25° C. for 4.5 hr., then diluted with ethyl acetate, The organic phase is washed with aqueous sodium bicarbonate and brine, dried over sodium sulfate, and concentrated to the crude title compound. The residue is chromatographed on silica gel, eluting with ethyl acetate-Skellysolve B, to yield the title compound. The corresponding 9,11-dideoxy-6ξ,9α-epoxymethano-6ξ-hydroxy-PGF$_1$ compound is also present in the equilibrium mixture.

EXAMPLE 26

9-Deoxy-9α-hydroxymethyl-6-keto-13,14-dihydro-PGF$_{1α}$, Methyl Ester (Formula I wherein X is —CH$_2$CH$_2$—) and 9-deoxy-9α-hydroxymethyl-6-keto-13,14-dihydro-PGF$_{1α}$ The 9-deoxy-9α-hydroxymethyl-6-keto-13,14-dihydro-PGF$_{1α}$, methyl ester is first prepared. A mixture of 9-deoxy-9α-hydroxymethyl-6-keto-PGF$_{1α}$, methyl ester (Example 12, 0.5 g.) and 100 mg. of 5% palladium-on-charcoal catalyst in 50 ml. of ethyl acetate is hydrogenated under slight pressure for 4 hr. The mixture is filtered and concentrated to an oil. The oil is chromatographed on silica gel, eluting with acetone-methylene chloride to yield the methyl ester.

A mixture of the above methyl ester (0.42 g.) in 20 ml. methanol with 8 ml. 3N aqueous sodium hydroxide is stirred at about 25° C. for 2 hr. The mixture is concentrated partially, acidified with aqueous potassium hydrogen sulfate solution and extracted with ethyl acetate. The extract is washed with brine, dried and concentrated. The residue is chromatographed on silica gel, eluting with ethyl acetate hexane to yield the acid title compound.

The above compounds, as their separate equilibrium mixtures, contain the corresponding 9-deoxy-6,9α-epoxymethano-6-hydroxy-13,14-dihydro-PGF$_1$ compounds.

EXAMPLE 27

(5Z)-9-Deoxy-6,9α-epoxymethano-Δ$^5$-13,14-dihydro-PGF$_1$, Methyl Ester (Formula IV: L is —(CH$_2$)$_3$—, Q is

R$_1$ is —COOCH$_3$, R$_4$ is n-pentyl,  is and X is —CH$_2$CH$_2$—).

Refer to Chart C. A solution of 9-deoxy-9α-hydroxymethyl-13,14-dihydro-(15RS)-PGF$_{2\alpha}$, methyl ester (0.250 g.) in 11 ml. of methylene chloride cooled in an ice bath is treated with N-bromosuccinimide (0.128 g.) and stirred for 0.5 hr. Then a solution of sodium sulfite (0.106 g. in 5 ml. water) is added. The mixture is washed with water and brine, dried over sodium sulfate, and concentrated. The residue consisting mainly of the 5-bromo intermediate, is dissolved in 15 ml. benzene and treated with 0.8 ml. of DBU. The mixture is heated at reflux 16 hr. It is then cooled, mixed with water and ice, and separated. The organic phase is extracted with ice water, then with water and brine, dried over sodium sulfate, and concentrated. The residue is chromatographed on silica gel pre-treated with ethyl acetate-Skellysolve B-triethylamine, eluting with ethyl acetate-Skellysolve B-0.1% triethylamine to yield the title compound.

EXAMPLE 28

5ξ-Bromo-9-deoxy-6ξ,9α-epoxymethano-13,14-didehydro-(15S)-PGF$_1$, Methyl Ester, less polar isomer and more polar isomer (Formula III: L is —(CH$_2$)$_3$—, Q is

R$_1$ is —COOCH$_3$, R$_4$ is n-pentyl, R$_{19}$ is bromo,  is

and X is —C≡C—).

Refer to Chart A. A solution of 9-deoxy-9α-hydroxymethyl-13,14-didehydro-PGF$_{2\alpha}$, methyl ester (0.35 g.) in 4 ml. of dioxane is treated with N-bromoacetamide (0.147 g.) at about 25° C. for about 30 min. The mixture is diluted with diethyl ether, washed with 0.5 M sodium thiosulfate and 5% sodium chloride, dried, filtered and concentrated to an oil (0.53 g.). The oil is combined with the product from a similar experiment (total 0.86 g.) and chromatographed on silica gel, eluting with acetonemethylene chloride. There are obtained the title compounds, first the less polar isomer, followed by the more polar isomer.

EXAMPLE 29

5ξ-Bromo-9-deoxy-6ξ,9α-epoxymethano-13,14-didehydro-(15R)-PGF$_1$, Methyl Ester, less polar isomer and more polar isomer (Formula III: L, R$_1$, R$_{19}$,  and X as for Example 25, and Q$_1$ is

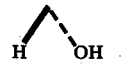).

Refer to Chart A. A solution of 9-deoxy-9α-hydroxymethyl-13,14-didehydro-(15R)-PGF$_{2\alpha}$, methyl ester (0.99 g.) in 10 ml. of dioxane is treated with N-bromoacetamide (0.414 g.) at about 25° C. for about 20 min. The mixture is washed with 0.5M sodium thiosulfate, 5% sodium chloride and 5% sodium bicarbonate, dried and concentrated to yield the mixed isomers of the title compound. The product is chromatographed on silica gel, eluting with acetone-methylene chloride to yield, first, the less polar isomer, followed by the more polar isomer.

EXAMPLE 30

9-Deoxy-9α-hydroxymethyl-6-keto-13,14-didehydro-PGF$_{1\alpha}$ (Formula I: Q is

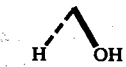

and X is —C≡C—) and 9-deoxy-9α-hydroxymethyl-6-keto-13,14-didehydro-(15R)-PGF$_{1\alpha}$ (Formula I: Q is

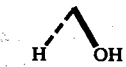

and X is —C≡C—).

Refer to Chart A. A solution of the more polar isomer of the 15-S product from Example 28 above (0.29 g.) in 5 ml. of dimethyl sulfoxide and 0.5 ml. of methanol is treated with potassium tert-butoxide (0.3 g.) for 20 hr. On hydrolysis of the methyl ester with 2 N. NaOH for 3 hr. followed by diluted with 5% sodium chloride, acidifying with 10% phosphoric acid, extraction with diethyl ether, washing with 5% sodium chloride, drying, and concentrating there is obtained 0.20 g. residue. The residue is subjected to silica gel chromatography, eluting with hexane-ethyl acetate to yield the 15S title compound.

Likewise, using the more polar isomer of the 15R intermediate of Example 29, there is obtained the corresponding 15R title compound.

Following the procedures of Example 30 but substituting sodium methoxide for potassium tert-butoxide there are likewise obtained the title compounds.

EXAMPLE 31

(5Z)-2-Decarboxy-2-hydroxymethyl-9-deoxy-6,9α-epoxymethano-Δ$^5$-PGF$_1$ (Formula IV: L is —(CH$_2$)$_3$—, Q is

R$_1$ is —CH$_2$OH, R$_4$ is n-pentyl,  is and trans—CH=CH—).

A mixture of (5Z)-9-deoxy-6,9α-epoxymethano-Δ$^5$-PGF$_1$, sodium salt (Example 15, 0.748 g.) in 60 ml. of tetrahydrofuran is treated with lithium aluminum hydride (0.152 g.) at −10° to −20° C., then allowed to warm to about 25° C. and stirred for 16 hr. The mixture is cooled to −10° to −20° C. and quenched with aqueous sodium sulfate, added dropwise. The mixture is diluted with tetrahydrofuran, dried over magnesium sulfate, and concentrated. The residue is chromatographed on a high pressure silica gel column of 40-60μ particle size, eluting with acetone-hexane-triethylamine to yield the title compound.

EXAMPLE 32

5ξ-Iodo-9-deoxy-6ξ,9α-epoxymethano-15-keto-PGF$_1$, Methyl Ester (Formula III: L is —(CH$_2$)$_3$—, Q is

R$_1$ is —COOCH$_3$, R$_4$ is n-pentyl, R$_{19}$ is iodo, R$_{21}$ is

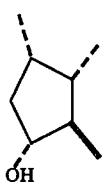

and X is trans—CH=CH—).

A solution of the formula-III 5ξ-iodo-9-deoxy-6,9α-epoxymethano-PGF$_1$, methyl ester (Example 11, 3.0 g.) in 100 ml. of acetone is cooled in a Dry Ice-methanol bath and treated with 4.5 ml. of Jones reagent (J. Chem. Soc. 39 (1946)) added dropwise over 5 min. The mixture is stirred for 45 min., then quenched with isopropanol and concentrated to one-third of its volume. The residue is taken up in ether, washed with brine, dried, and concentrated. The residue is chromatographed on silica gel, eluting with acetone-methylene chloride to obtain the title compound.

EXAMPLE 33

(5Z)-9-Deoxy-6,9α-epoxymethano-Δ$^5$-15-keto-PGF$_1$, Methyl Ester (Formula IV: Q is

Refer to Chart C. A solution of the formula-XIII 5ξ-iodo-9-deoxy-6,9α-epoxymethano-15-keto-PGF$_1$, methyl ester (Example 32, 0.75 g.) in 7.5 ml. of toluene is treated with 1.0 ml. of DBU at about 25° C. for 22 hr. The mixture is washed with ice-water and the aqueous phase is back-washed with diethyl ether. The organic phases are combined, washed with ice-cold brine, dried and concentrated. The residue, 0.48 g., is chromatographed on Florisil ® pretreated with ethyl acetate-Skellysolve B-triethylamine, eluting with ethyl acetate-Skellysolve B to yield the title compound.

EXAMPLE 34

(5Z)-9-Deoxy-6,9α-epoxymethano-Δ$^5$-PGF$_1$, Amide (Formula IV: L is —(CH$_2$)$_3$—, Q is

R$_1$ is

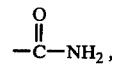

R$_4$ is n-pentyl, 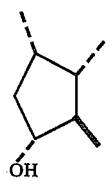 is and X is trans—CH=CH—).

Refer to Chart C. A solution of the formula-XIII 5ξ-iodo-9-deoxy-6ξ,9α-epoxymethano-PGF$_1$, amide (Example 1, 2.46 g.) in 125 ml. of benzene is treated with 5 ml. of DBN in 5 ml. of methylene chloride at 40-45° C. for about 16 hr. The mixture is cooled, diluted with ice water, and extracted with benzene and methylene chloride, keeping a few drops of triethylamine in the organic phase. The combined organic phases are washed with ice water, dried, and concentrated. The residue is purified by chromatography on Florisil ® to yield the title compound.

EXAMPLE 35

(5Z)-9-Deoxy-6,9α-epoxymethano-Δ$^5$-PGF$_1$, Methylamide (Formula IV: L, Q, R$_4$, R$_{20}$ and X are as in Example 34, and R$_1$ is —C(O)NHCH$_3$).

Refer to Chart C. A solution of the formula-XIII 5ξ-iodo-9-deoxy-6ξ,9α-epoxymethano-PGF₁, N-methylamide, mixed isomers (Example 2, 1.2 g.) in 75 ml. of benzene is treated with 3 ml. of DBN at 40° C. for 24 hr. and then at reflux for 3 hr. The mixture is cooled, diluted with 25 ml. of benzene and washed with ice water. The organic phase is dried over sodium sulfate and concentrated. The residue is purified by chromatography on Florisil ® to yield the title compound.

EXAMPLE 36

(5Z)-9-Deoxy-6,9α-epoxymethano-Δ⁵-PGF₁, n-Butylamide (Formula IV: L, Q, R₄, $\widehat{R_{20}}$, and X are as in Example 34 and R₁ is —C(O)NHC₄H₉).

Refer to Chart C. A solution of 5ξ-iodo-6ξ,9α-epoxymethano-PGF₁ n-butylamide (Example 3, 3.5 g.) in 100 ml. of benzene is treated with 8 ml. of DBN at 40°-45° C. for about 16 hr. The mixture is cooled, diluted with ice water, and extracted with chloroform, keeping a few drops of triethylamine in the organic phase. The combined organic phases are washed with ice water, dried and concentrated. The residue is chromatographed on Florisil ® to yield the title compound.

EXAMPLE 37

(5Z)-9-Deoxy-6,9α-epoxymethano-Δ⁵-PGF₁, Anilide (Formula IV: L, Q, R₄, $\widehat{R_{20}}$ and X are as in Example 34 and R₁ is —C(O)NHC₆H₅).

Refer to Chart C. A solution of 9-deoxy-6ξ,9α-epoxymethano-PGF₁, anilide (Example 5, 1.8 g.) in 100 ml. of benzene is treated with 4 ml. of DBN at 40° C. for 22 hr. Thereafter the mixture is cooled to about 25° C., diluted with 50 ml. of benzene, and washed with ice water. The organic phase is dried over sodium sulfate, treated with 1 ml. of triethylamine, and concentrated. The residue is purified by chromatography on Florisil ® to yield the title compound.

EXAMPLE 38

(5Z)-9-Deoxy-6,9α-epoxymethano-Δ⁵-PGF₁, Benzylamide (Formula IV: L, Q, R₄, $\widehat{R_{20}}$ and X are as in Example 34 and R₁ is —C(O)NHCH₂C₆H₅).

Refer to Chart C. A solution of 5ξ-iodo-6ξ,9α-epoxymethano-PGF₁ benzylamide (Example 4, 1.8 g.) in 100 ml. of benzene is treated with 4 ml. of DBN at about 40° C. for 22 hr. The mixture is cooled, diluted with 50 ml. of benzene and washed with ice water. The organic phase is dried and concentrated to yield the title compound.

EXAMPLE 39

9-Deoxy-9α-hydroxymethyl-6-keto-PGF₁α, Amide (Formula I: L is —(CH₂)₃—, Q is

R₁ is —C(O)NH₂, R₄ is n-pentyl, $\widehat{R_{20}}$ is

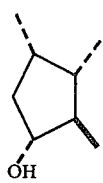

and X is trans—CH═CH—), and 9-deoxy-6,9α-epoxymethano-6ξ-hydroxy-PGF₁, Amide (Formula II).

A solution of (5Z)-9-deoxy-6,9α-epoxymethano-Δ⁵-PGF₁, amide (Example 34, 2.0 g.) in 50 ml. of tetrahydrofuran is treated with 3 ml. of 10% potassium hydrogen sulfate. After 10-20 min. the mixture is concentrated. The residue is taken up in water and ethyl acetate. The solution is saturated with sodium chloride and diluted with acetone (equal in volume to one-fifth of the ethyl acetate). The organic phase is separated and the aqueous phase again extracted with ethyl acetate. The combined organic phases are washed with brine, dried, and concentrated. The residue is chromatographed on silica gel, eluting with acetone-methylene chloride to yield a mixture of the title compounds.

EXAMPLE 40

9-Deoxy-9α-hydroxymethyl-6-keto-PGF₁, Methylamide (Formula I: L, Q, R₄, $\widehat{R_{20}}$ and X are as in Example 38, and R₁ is —C(O)NHCH₃), and 9-Deoxy-6,9α-epoxymethano-6ξ-hydroxy-PGF₁, Methylamide (Formula II).

A solution of the formula-IV (5Z)-9-deoxy-6,9α-epoxymethano-Δ⁵-PGF₁, methylamide (Example 35, 0.29 g.) in 5 ml. of tetrahydrofuran is treated with about 1 ml. of 5% aqueous hyrochloric acid and stirred at 25° C. for one hour. The mixture is diluted with 50 ml. of brine and extracted with ethyl acetate. The organic phase is washed with saturated aqueous sodium bicarbonate and brine, dried over sodium chloride, and concentrated. A second lot is prepared in the same way and the two products are combined for chromatography on silica gel. Eluting with acetone-methylene chloride yields the title compound.

EXAMPLE 41

9-Deoxy-9α-hydroxymethyl-6-keto-PGF₁ n-Butylamide (Formula I: L, Q, R₄, $\widehat{R_{20}}$ and X are as in Example 38 and R₁ is —C(O)NHC₄H₉), and 9-Deoxy-6,9α-epoxy-6-hydroxy-PGF₁, n-Butylamide (Formula II).

A solution of (5Z)-9-deoxy-6,9α-epoxymethano-Δ⁵-PGF₂, n-butylamide, Example 36, 3.0 g.) in 25 ml. of tetrahydrofuran is treated with sufficient 10% aqueous potassium hydrogen sulfate solution to bring the pH to 5.0. The mixture is concentrated to remove tetrahydrofuran and the residue is taken up in water and ethyl acetate. Sodium chloride is added to saturation and the organic phase is separated. The aqueous phase is extracted with acetoneethyl acetate (1:4) and the organic phases are combined. The organic phases are washed with brine, dried, and concentrated. The residue is chromatographed on silica gel, eluting with acetone-methylene chloride to yield a mixture of the title compounds.

EXAMPLE 42

9-Deoxy-9α-hydroxymethyl-6-keto-PGF₁, Benzylamide (Formula I: L, Q, R₄, $\widehat{R_{20}}$ and X are as in Example 38 and R₁ is —C(O)NHCH₂C₆H₅), and 9-Deoxy-6,9α-epoxymethano-6-hydroxy-PGF₁, Benzylamide (Formula II).

I. There is first prepared the formula-III bis(THP) ether. A solution of the formula-III 5ξ-iodo-9-deoxy-6ξ,9α-epoxymethano-PGF₁, benzylamide (Example 4, 2.0 g.) in 30 ml. of methylene chloride with 2.5 ml. of dihydropyran and 25 mg. of p-toluenesulfonic acid monohydrate is stirred at 25° C. for 25 min. The mixture is diluted with 100 ml. of methylene chloride and washed with 25 ml. of saturated aqueous sodium bicarbonate solution and 25 ml. of brine. The organic phase is dried over sodium sulfate and concentrated. The residue is chromatographed on silica gel eluting with acetone-methylene chloride to yield the bis(THP) ether.

II. There is next prepared the formula-IV enol ether, N-benzylamide, bis(THP) ether. A solution of the bis(THP) ether above, 2.4 g. in 100 ml. of benzene is stirred with 4 ml. of DBN at 40°–45° C. for 22 hr. The mixture is cooled, diluted with 25 ml. of benzene, and washed with 25 ml. of ice water. The organic phase is dried and concentrated. The residue consists of the enol ether, i.e. (5Z)-9-deoxy-6,9α-epoxymethano-Δ$^5$-PGF$_1$, benzylamide, bis(THP) ether. It is treated with a solution of 45 ml. of tetrahydrofuran and 5 ml. of 5% aqueous hydrochloric acid at about 25° C. for 15 min. The mixture is diluted with 50 ml. of brine and extracted with ethyl acetate. The organic phase is washed with brine, dried, and concentrated to yield the bis(THP) ether of the title compound.

III. The title compound is obtained by hydrolytic removal of the THP groups. The product of part II, 1.0 g., is treated with 20 ml. of acetic acid-water-tetrahydrofuran (20:10:3) at 40°–45° C. for 3.5 hours. The mixture is diluted with 30 ml. of water and freeze-dried. The residue is dissolved in methylene chloride and chromatographed on Florisil ®. Elution with acetone-methylene chloride yields the title compound.

EXAMPLE 43

(5R,6R)-5-Iodo-9-deoxy-6,9α-epoxymethano-17,18-didehydro-PGF$_1$, Methyl Ester and (5S,6S)-5-Iodo-9-deoxy-6,9α-epoxymethano-17,18-didehydro-PGF$_1$, Methyl Ester (Formula III: R$_4$ is

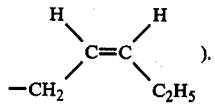

).

Refer to Chart A. A solution of 9-deoxy-9α-hydroxymethyl-PGF$_{3α}$, methyl ester (1.3 g.) in 166 ml. of methylene chloride is stirred with 26 ml. of a saturated aqueous solution of sodium bicarbonate. To the mixture is added dropwise, within 35 min., a solution of iodine (38 ml., 2.5%) in methylene chloride at about 25° C. After one hour, the reaction mixture is diluted with 600 ml. of methylene chloride and is washed with 30 ml. of 0.25 M aqueous sodium thiosulfate. The organic phase is washed successively with water (180 ml.), pH 2 buffer solution (70 ml.), and water (180 ml.). The organic phase is dried over magnesium sulfate and concentrated. The residue is chromatographed on silica gel eluting with acetone-hexane, There is thus obtained (5S,6S)-5-iodo-9-deoxy-6,9α-epoxymethano-17,18-didehydro-PGF$_1$, methyl ester, and, second, (5R,6R)-5-iodo-9-deoxy-6,9α-epoxymethano-17,18-didehydro-PGF$_1$, methyl ester.

EXAMPLE 44

(5Z)-9-Deoxy-6,9α-epoxymethano-Δ$^5$-17,18-didehydro-PGF$_1$, Methyl Ester) (Formula IV: R$_4$ is

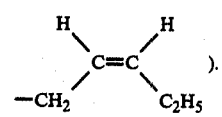

).

Refer to Chart C. A solution of (5R,6R)-5-iodo-9-deoxy-6,9α-epoxy-17,18-didehydro-PGF$_1$, methyl ester, (Example 42, 230 mg.) and 1,5-diazabicyclo[4.3.0]-non-5-ene (0.4 ml.) in 10 ml. of benzene is heated under nitrogen at 40°–45° C. for 48 hr. The reaction is cooled to about 25° C., diluted with benzene, and washed with water (two 8 ml. portions). The organic phase is dried over sodium sulfate, filtered, and concentrated. The residue is chromatographed on Florisil ® (10 g.), using acetone-hexane (containing 0.1% triethylamine) as the eluting solvent. There is obtained the title compound.

EXAMPLE 45

(5Z)-9-Deoxy-6,9α-epoxymethano-Δ$^5$-17,18-didehydro-PGF$_1$, Sodium Salt.

A solution of (5Z)-9-deoxy-6,9α-epoxymethano-Δ$^5$-17,18-didehydro-PGF$_1$, methyl ester, (Example 44, 100 mg.) in 8 ml. of methanol and 3 ml. of water is treated with dilute aqueous sodium hydroxide at intervals over a period of 72 hours until the starting material is entirely consumed as evidenced by TLC. Excess methanol is removed under reduced pressure. The remaining aqueous solution is frozen and subjected to lyophilization to yield a white powder containing the title compound.

EXAMPLE 46

9-Deoxy-9α-hydroxymethyl-6-keto-17,18-didehydro-PGF$_1$, Methyl Ester (Formula I: R$_4$ is

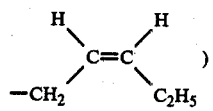

)

and 9-Deoxy-6ξ,9α-epoxymethano-6ξ-hydroxy-17,18-didehydro-PGF$_1$, Methyl Ester (Formula II).

A solution of (5Z)-9-deoxy-6,9α-epoxymethano-Δ$^5$-17,18-didehydro-PGF$_1$, methyl ester, (Example 44, 100 mg.) in tetrahydrofuran (10 ml.) and pH 2 buffer (10 ml.) is stirred at about 25° C. for 30 min. Brine (10 ml.) is added and the resulting mixture is extracted four times with ethyl acetate. The organic phase is dried over magnesium sulfate and concentrated. The residue is chromatographed (HPLC) on silica gel (22 g.) using acetone-hexane as the eluting solvent to give a mixture of the title compounds.

EXAMPLE 47

9-Deoxy-9α-hyroxymethyl-6-keto-17,18-didehydro-PGF$_1$ (Formula I) and 9-Deoxy-≠ξ,9α-epoxymethano-6ξ-hydroxy-17,18-didehydro-PGF$_1$ ( Formula II).

A solution of 9-deoxy-9α-hydroxymethyl-6-keto-17,18-didehydro-PGF$_1$, methyl ester and 9-deoxy-6ξ,9α-epoxymethano-6ξ-hydroxy-17,18-didehydro-PGF$_1$, methyl ester (Example 46, 100 mg.) in methanol (8 ml.) and water (3 ml.) is treated with dilute aqueous sodium hydroxide sufficient to saponify the ester function. The excess methanol is removed under reduced pressure. The remaining aqueous solution is acidified to pH 2 and extracted with ethyl acetate. Drying the or-

EXAMPLE 48

5ξ-Iodo-9-deoxy-6ξ,9α-epoxymethano-15-deoxy-PGF$_1$, Methyl Ester (Formula XIII: Q$_1$ is

H  H ).

Refer to Chart C. A solution of 9-deoxy-9α-hydroxymethyl-15-deoxy-PGF$_2$, methyl ester (0.4 g.) in 55 ml. of methylene chloride is mixed with 9 ml. of saturated aqueous sodium bicarbonate and treated with 12.2 ml. of 2.5% solution of iodine in methylene chloride, added dropwise over 5 min. at about 25° C. The mixture is stirred for one hr., then mixed with 200 ml. of cold 0.25 N. sodium thiosulfate solution to decolorize, saturated with sodium chloride, and extracted with methylene chloride. The organic phase is washed with brine containing pH 2 buffer, dried, and concentrated to the title compound.

EXAMPLE 49

(5Z)-9-Deoxy-6,9α-epoxymethano-Δ$^5$-15-deoxy-PGF$_1$, Methyl Ester (Formula IV: Q is

H  H ).

Refer to Chart C. A solution of 5ξ-iodo-9-deoxy-6ξ,9α-epoxymethano-15-deoxy-PGF$_1$, methyl ester (Example 48, 0.55 g.) in 30 ml. of benzene is treated with 1.2 ml. of DBN added at about 25° C. and warmed to 50° C. for 5 hr. The mixture is then left about 25° C. for 16 hr., poured into cold ethyl acetate and brine, and separated. The aqueous phase is extracted with ethyl acetate. The combined organic phases are washed with brine, dried over sodium sulfate, and concentrated. The residue is chromatographed on Florisil ® pretreated with ethyl acetate-hexanetriethylamine (2.5%), eluting with the same solvent to yield the title compound.

EXAMPLE 50

(5Z)-9-Deoxy-6,9α-epoxymethano-Δ$^5$-15-deoxy-PGF$_1$, Sodium Salt

A mixture of (5Z)-9-deoxy-6,9α-epoxymethano-Δ$^5$-15-deoxy-PGF$_1$, methyl ester (Example 49, 0.28 g.) in 10 ml. of methanol is treated cautiously with a solution of sodium carbonate (0.28 g.) in 5 ml. of water and thereafter stirred at about 25° C. for 90 hr. The mixture is concentrated to 5 ml. volume, diluted with 20 ml. of acetonitrile, and, after 15 min., filtered. The filtrate is concentrated, and azeotroped with aceotonitrile, to yield the title compound.

EXAMPLE 51

(5Z)-9-Deoxy-6,9α-epoxymethano-Δ$^5$-17-phenyl-18,19,20-trinor-PGF$_1$, Methyl Ester (Formula IV: R$_4$ is

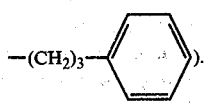

Refer to Chart C. Following the procedures of Example 32 but replacing the iodo ether of that example with 5ξ-iodo-9-deoxy-6ξ,9α-epoxymethano-17-phenyl-18,19,20-trinor-PGF$_1$, methyl ester (Preparation 9) there is obtained the title compound.

On treating the above compound in tetrahydrofuran solution with pH 2 buffer at about 25° C. for 30 min. and following the procedures of Example 45, there is obtained a mixture of 9-deoxy-9α-hydroxymethyl-6-keto-17-phenyl-18,19,20-trinor-PGF$_{1α}$, methyl ester and 9-deoxy-6ξ,9α-epoxymethano-6ξ-hydroxy-17-phenyl-18,19,20-trinor-PGF$_1$, methyl ester.

Following the procedures of Examples 11, 12, and 15 as illustrated by Charts A and C, but employing appropriate starting materials corresponding to formulas IX or XII, there are prepared the formula-I, -II, -III, and -IV compounds, namely
9-deoxy-9α-hydroxymethyl-6-keto-PGF$_{1α}$,
9-deoxy-6ξ,9α-epoxymethano-6ξ-hydroxy-PGF$_1$,
5ξ-halo-9-deoxy-6ξ,9α-epoxymethano-PGF$_1$, and
(5Z)-9-deoxy-6,9α-epoxymethano-Δ$^5$-PGF$_1$-type compounds,
in methyl ester form wherein R$_1$ is —COOCH$_3$, having the following structural features:

16-Methyl-;
16,16-Dimethyl-;
16-Fluoro-;
16,16-Difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
16-Methyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenoxy-17,18,19,20-tetranor-13,14-didehydro-;
16-(m-trifluoromethylphenoxy-17,18,19,20-tetranor-13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;

16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
16-Methyl-cis-13;
16,16-Dimethyl-cis-13-;
16-Fluoro-cis-13-;
16,16-Difluoro-cis-13-;
17-Phenyl-18,19,20-trinor-cis-13-;
17-(m-trifluoromethylphenyl)-18,19,20-trinor-cis-13-;
17-(m-chlorophenyl)-18,19,20-trinor-cis-13-;
17-(p-fluorophenyl)-18,19,20-trinor-cis-13-;
16-Methyl-17-phenyl-18,19,20-trinor-cis-13-;
16,16-Dimethyl-17-phenyl-18,19,20-trinor-cis-13-;
16-Fluoro-17-phenyl-18,19,20-trinor-cis-13-;
16,16-Difluoro-17-phenyl-18,19,20-trinor-cis-13-;
16-Phenoxy-17,18,19,20-tetranor-cis-13-;
16-(m-trifluoromethylphenoxy)-17,18,19,20-tetranor-cis-13-;
16-(m-chlorophenoxy)-17,18,19,20-tetranor-cis-13-;
16-(p-fluorophenoxy)-17,18,19,20-tetranor-cis-13-;
16-Phenoxy-18,19,20-trinor-cis-13-;
16-Methyl-16-phenoxy-18,19,20-trinor-cis-13-;
2,2-Difluoro-;
2,2-Difluoro-16-methyl-;
2,2-Difluoro-16,16-dimethyl-;
2,2-Difluoro-16-fluoro;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-methyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenoxy-17,18,19,20-tetranor-;
2,2-Difluoro-16-(m-trifluoromethylphenoxy;-17,18,19,20-tetranor-;
2,2-Difluoro-16-(m-chlorophenoxy)-17,18,19,20-tetranor-;
2,2-Difluoro-16-(p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-16-methyl-16-phenoxy-18,19,20-trinor-;
2,2-Difluoro-16-methyl-13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-phenoxy-18,19,20-trinor-13,14-dihydro-;
2,2-Difluoro-16-methyl-16-phenoxy-18,19,20-trinor-13,14-dihydro-;
2,2-Difluoro-cis-13-;
2,2-Difluoro-16-methyl-cis-13-;
2,2-Difluoro-16,16-dimethyl-cis-13-;
2,2-Difluoro-16-fluoro-cis-13-;
2,2-Difluoro-16,16-difluoro-cis-13-;
2,2-Difluoro-17-phenyl-18,19,20-trinor-cis-13-;
2,2-Difluoro-17-(m-trifluoromethylphenyl)-18,19,20-trinor-cis-13-;

2,2-Difluoro-17-(m-chlorophenyl)-18,19,20-trinor-cis-13-;
2,2-Difluoro-17-(p-fluorophenyl)-18,19,20-trinor-cis-13-;
2,2-Difluoro-16-methyl-17-phenyl-18,19,20-trinor-cis-13-;
2,2-Difluoro-16,16-dimethyl-17-phenyl-18,19,20-trinor-cis-13-;
2,2,16-Trifluoro-17-phenyl-18,19,20-trinor-cis-13-;
2,2,16,16-Tetrafluoro-17-phenyl-18,19,20-trinor-cis-13-;
2,2-Difluoro-16-phenoxy-17,18,19,20-tetranor-cis-13-;
2,2-Difluoro-16-(m-trifluoromethylphenoxy)-17,18,19,20-tetranor-cis-13-;
2,2-Difluoro-16-(m-chlorophenoxy)-17,18,19,20-tetranor-cis-13-;
2,2-Difluoro-16-(p-fluorophenoxy)-17,18,19,20-tetranor-cis-13-;
2,2-Difluoro-16-phenoxy-18,19,20-trinor-cis-13-;
2,2-Difluoro-16-methyl-16-phenoxy-18,19,20-trinor-cis-13-;
3-Oxa-;
3-Oxa-16-methyl-;
3-Oxa-16,16-dimethyl-;
3-Oxa-16-fluoro-;
3-Oxa-16,16-difluoro-;
3-Oxa-17-phenyl-18,19,20-trinor-;
3-Oxa-17-(m-trifluoromethylphenyl)-18,19,20-trinor-;
3-Oxa-17-(m-chlorophenyl)-18,19,20-trinor-;
3-Oxa-17-(p-fluorophenyl)-18,19,20-trinor-;
3-Oxa-16-methyl-17-phenyl-18,19,20-trinor-;
3-Oxa-16,16-dimethyl-17-phenyl-18,19,20-trinor-;
3-Oxa-16-fluoro-17-phenyl-18,19,20-trinor-;
3-Oxa-16,16-difluoro-17-phenyl-18,19,20-trinor-;
3-Oxa-16-phenoxy-17,18,19,20-tetranor-;
3-Oxa-16-(m-trifluoromethylphenoxy)-17,18,19,20-tetranor-;
3-Oxa-16-(m-chlorophenoxy)-17,18,19,20-tetranor-;
3-Oxa-16-(p-fluorophenoxy)-17,18,19,20-tetranor-;
3-Oxa-16-phenoxy-18,19,20-trinor-;
3-Oxa-16-methyl-16-phenoxy-18,19,20-trinor-;
3-Oxa-13,14-didehydro-;
3-Oxa-16-methyl-13,14-didehydro-;
3-Oxa-16,16-dimethyl-13,14-didehydro-;
3-Oxa-16-fluoro-13,14-didehydro-;
3-Oxa-16,16-difluoro-13,14-didehydro-;
3-Oxa-17-phenyl-18,19,20-trinor-13,14-didehydro-;
3-Oxa-17-(m-trifluoromethylphenyl)-18,19,20-trinor-13,14-didehydro-;
3-Oxa-17-(m-chlorophenyl)-18,19,20-trinor-13,14-didehydro-;
3-Oxa-17-(p-fluorophenyl)-18,19,20-trinor-13,14-didehydro-;
3-Oxa-16-methyl-17-phenyl-18,19,20-trinor-13,14-didehydro-;
3-Oxa-16,16-dimethyl-17-phenyl-18,19,20-trinor-13,14-didehydro-;
3-Oxa-16-fluoro-17-phenyl-18,19,20-trinor-13,14-didehydro-;
3-Oxa-16,16-difluoro-17-phenyl-18,19,20-trinor-13,14-didehydro-;
3-Oxa-16-phenoxy-17,18,19,20-tetranor-13,14-didehydro-;
3-Oxa-16-(m-trifluoromethylphenoxy)-17,18,19,20-tetranor-13,14-didehydro-;
3-Oxa-16-(m-chlorophenoxy)-17,18,19,20-tetranor-13,14-didehydro-;
3-Oxa-16-phenoxy-18,19,20-trinor-13,14-didehydro-;
3-Oxa-16-methyl-16-phenoxy-18,19,20-trinor-13,14-didehydro-;
3-Oxa-13,14-dihydro-;
3-Oxa-16-methyl-13,14-dihydro-;
3-Oxa-16,16-dimethyl-13,14-dihydro-;
3-Oxa-16-fluoro-13,14-dihydro-;
3-Oxa-16,16-difluoro-13,14-dihydro-;
3-Oxa-17-phenyl-18,19,20-trinor-13,14-dihydro-;
3-Oxa-17-(m-trifluoromethylphenyl)-18,19,20-trinor-13,14-dihydro-;
3-Oxa-17-(m-chlorophenyl)-18.19,20-trinor-13,14-dihydro-;
3-Oxa-17-(p-fluorophenyl)-18,19,20-trinor-13,14-dihydro-;
3-Oxa-16-methyl-17-phenyl-18,19,20-trinor-13,14-dihydro-;
3-Oxa-16,16-Dimethyl-17-phenyl-18,19,20-trinor-13,14-dihydro-;
3-Oxa-16-fluoro-17-phenyl-18,19,20-trinor-13,14-dihydro-;
3-Oxa-16,16-difluoro-17-phenyl-18,19,20-trinor-13,14-dihydro-;
3-Oxa-16-phenoxy-17,18,19,20-tetranor-13,14-dihydro-;
3-Oxa-16-(m-trifluoromethylphenoxy)-17,18,19,20-tetranor-13,14-dihydro-;
3-Oxa-16-(m-chlorophenoxy)-17,18,19,20-tetranor-13,14-dihydro-;
3-Oxa-16-(p-fluorophenoxy)-17,18,19,20-tetranor-13,14-dihydro-;
3-Oxa-16-phenoxy-18,19,20-trinor-13,14-dihydro-;
3-Oxa-16-methyl-16-phenoxy-18,19,20-trinor-13,14-dihydro-;
3-Oxa-cis-13-;
3-Oxa-16-methyl-cis-13-;
3-Oxa-16,16-dimethyl-cis-13-;
3-Oxa-16-fluoro-cis-13-;
3-Oxa-16,16-difluoro-cis-13-;
3-Oxa-17-phenyl-18,19,20-trinor-cis-13-;
3-Oxa-17-(m-trifluoromethylphenyl)-18,19,20-trinor-cis-13-;
3-Oxa-17-(m-chlorophenyl)-18,19,20-trinor-cis-13-;
3-Oxa-17-(p-fluorophenyl)-18,19,20-trinor-cis-13-;
3-Oxa-16-methyl-17-phenyl-18,19,20-trinor-cis-13-;
3-Oxa-16,16-dimethyl-17-phenyl-18,19,20-trinor-cis-13-;
3-Oxa-16-fluoro-17-phenyl-18,19,20-trinor-cis-13-;
3-Oxa-16,16-difluoro-17-phenyl-18,19,20-trinor-cis-13-;
3-Oxa-16-phenoxy-17,18,19,20-tetranor-cis-13-;
3-Oxa-16-(m-trifluoromethylphenoxy)-17,18,19,20-tetranor-cis-13-;
3-Oxa-16-(m-chlorophenoxy)-17,18,19,20-tetranor-cis-13-;
3-Oxa-(p-fluorophenoxy)-17,18,19,20-tetranor-cis-13-;
3-Oxa-16-phenoxy-18,19,20-trinor-cis-13-;
3-Oxa-16-methyl-16-phenoxy-18,19,20-trinor-cis-13-;

Likewise following the procedures of Examples 11, 12, and 15, but employing corresponding starting materials, there are obtained the formula -I, -II, -III, and -IV compounds, namely
9-deoxy-9α-hydroxymethyl-6-keto-PGF$_1$-,
9-deoxy-6ξ,9α-epoxymethano-6ξ-hydroxy-PGF$_1$-.
5ξ-halo-9-deoxy-6ξ,9α-epoxymethano-PGF$_1$-, and
(5Z)-9-deoxy-6,9α-epoxymethano-Δ$^5$-PGF$_1$-type compounds,
in methyl ester form wherein R$_1$ is —COOCH$_3$, having the following structural features:
2,3-Didehydro-;
2,2-Dimethyl-;
2a,2b-Dihomo-;

4-Oxa-4a-homo-;
11-Deoxy-10,11-didehydro-;
11β-;
11-Deoxy-11-keto-;
11-Deoxy-;
11-Deoxy-11-methylene-;
11-Deoxy-11-hydroxymethyl-;
15β-;
15-Keto-;
15-Deoxy-;
15-Methyl-15(S)-;
15-Methyl-15(R)-; and
17,18-Didehydro-.

I claim:

1. A 5Z compound of the formula

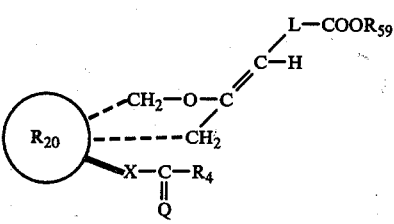

wherein $R_{20}$ is

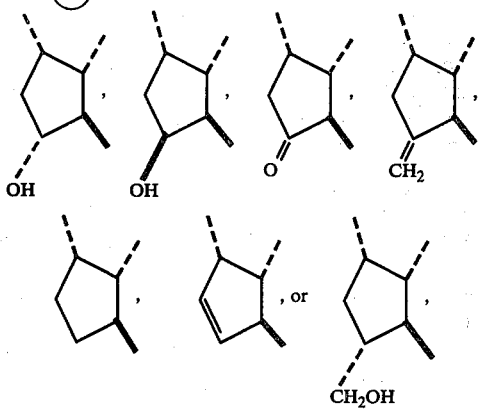

wherein L is
(1) —$(CH_2)_d$—$C(R_2)_2$—
(2) —$CH_2$—O—$CH_2$—Y— or
(3) —$CH_2CH=CH$— wherein $d$ is zero to 5, $R_2$ is hydrogen, methyl, or fluoro, being the same or different with the proviso that one $R_2$ is not methyl when the other is fluoro, and Y is a valence bond, —$CH_2$— or —$(CH_2)_2$—, wherein Q is

wherein $R_8$ is hydrogen or alkyl of one to 4 carbon atoms, inclusive,
wherein $R_{59}$ is (a) hydrogen, (b) alkyl of one to 12 carbom atoms, inclusive, or (c) a pharmacologically acceptable cation; wherein $R_4$ is

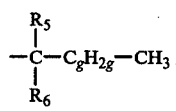

wherein $C_gH_{2g}$ is alkylene of one to 9 carbon atoms, inclusive, with one to 5 carbon atoms, inclusive, in the chain between —$CR_5R_6$— and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro; and
wherein X is
(1) trans-CH=CH—
(2) cis—CH=CH—
(3) —C≡C— or
(4) —$CH_2CH_2$—;
including the lower alkanoates thereof.

2. A compound according to claim 1 wherein $R_{20}$ is

3. A compound according to claim 1 wherein $R_{20}$ is

4. A compound according to claim 1 wherein $R_{20}$ is

5. A compound according to claim 1 wherein $R_{20}$ is

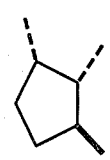

6. A compound according to claim 5 wherein L is —$(CH_2)_n$—, $n$ being 3, 4, or 5, wherein Q is

wherein $R_8$ is limited to hydrogen, methyl, or ethyl, and wherein $R_4$ is n-pentyl, 1,1-dimethylpentyl, or 1,1-difluoropentyl.

7. (5Z)-9-Deoxy-6,9α-epoxy-methano-$\Delta^5$-11-deoxy-PGF$_1$, methyl ester, a compound according to claim 6.

8. A compound according to claim 1 wherein $R_{20}$ is

9. A compound according to claim 1 wherein $R_{20}$ is

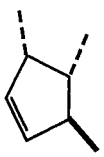

10. A compound according to claim 1 wherein $R_{20}$ is

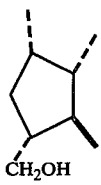

11. A compound according to claim 10 wherein L is —(CH$_2$)$_n$—, n being 3, 4, or 5, wherein Q is

wherein R$_8$ is hydrogen, methyl, or ethyl, and wherein R$_4$ is n-pentyl, 1,1-dimethylpentyl, or 1,1-difluoropentyl.

12. A compound according to claim 11 wherein X is —C≡C—.

13. A compound according to claim 11 wherein X is —CH$_2$CH$_2$—.

14. (5Z)-9-Deoxy-6,9α-epoxy-methano-Δ$^5$-13,14-didehydro-PGF$_1$, methyl ester, a compound according to claim 13.

15. A compound according to claim 11 wherein X is trans—CH=CH—.

16. A compound according to claim 15, wherein R$_{59}$ is hydrogen, methyl, or a pharmacologically acceptable cation.

17. (5Z)-9-Deoxy-6,9α-epoxy-methano-Δ$^5$-PGF$_1$, methyl ester, a compound according to claim 16.

18. (5Z)-9-Deoxy-6,9α-epoxymethano-Δ$^5$-PGF$_1$, methyl ester, 11,15-diacetate, a compound according to claim 16.

19. (5Z)-9-Deoxy-6,9α-epoxymethano-Δ$^5$-PGF$_1$, sodium salt, a compound according to claim 16.

20. (5Z)-9-Deoxy-6,9α-epoxymethano-Δ$^5$-15-keto-PGF$_1$, methyl ester, a compound according to claim 16.

21. (5Z)-9-Deoxy-6,9α-epoxymethano-Δ$^5$-15-deoxy-PGF$_1$, methyl ester, a compound according to claim 16.

22. A 5E compound of the formula

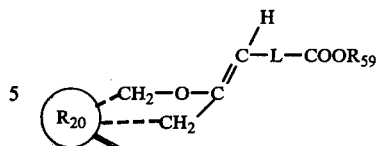

wherein $R_{20}$ is

wherein L is
(1) —(CH$_2$)$_d$—C(R$_2$)$_2$—
(2) —CH$_2$—O—CH$_2$—Y— or
(3) —CH$_2$CH=CH—
wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein Q is

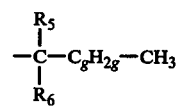

wherein R$_8$ is hydrogen or alkyl of one to 4 carbon atoms, inclusive,
wherein R$_{59}$ is (a) hydrogen, (b) alkyl of one to 12 carbon atoms, inclusive, or (c) a pharmacologically acceptable cation,
wherein R$_4$ is $$-\underset{R_6}{\overset{R_5}{\underset{|}{\overset{|}{C}}}}-C_gH_{2g}-CH_3$$

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different; and
wherein X is
(1) trans—CH=CH—
(2) cis—CH=CH—
(3) —C≡C— or
(4) —CH$_2$CH$_2$—;
including the lower alkanoates thereof.

23. (5E)-9-Deoxy-6,9α-epoxymethano-Δ$^5$-PGF$_1$, methyl ester, a compound according to claim 22.

* * * * *

UNITED STATES PATENT AND TRADEMARK OFFICE
CERTIFICATE OF CORRECTION

PATENT NO. : 4,124,599

DATED : 7 November 1978

INVENTOR(S) : Robert C. Kelly

It is certified that error appears in the above—identified patent and that said Letters Patent is hereby corrected as shown below:

column 1, the second formula should read as follows instead of as in the patent:

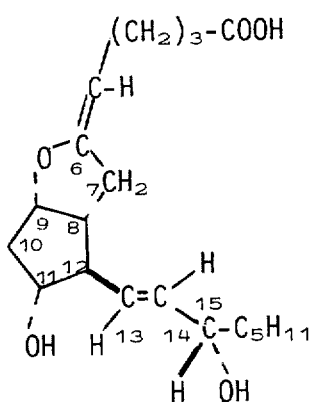

Column 7, line 1, "weight or per kg." should read -- weight or by intravenous infusion at a dose in the range 0.1 to 20 µg. per kg. --.
Column 8, line 28, "(1) $-(CH_2)-C(R_2)_2-$" should read -- (1) $-(CH_2)_d-C(R_2)_2-$ --.
Column 9, line 63, "$C_jz_j$" should read -- $C_jH_{2j}$ --.
Column 19, line 45, "$Q_1$" should read -- Q --.
Column 22, line 62, ", $-CH(CH_3)-$," should read -- , $-CH(CH_3)-CH(CH_3)-$, --.
Column 28, line 35, "X and - have" should read -- X and $\sim$ have --.
Column 33, line 64, "$-C=C-$" should read -- $-C\equiv C-$ --.
Column 33, line 65, "$-C=C-$" should read -- $-C\equiv C-$ --.
Column 34, line 47, "wherein $K_{33}$" should read -- wherein $R_{33}$ --.

UNITED STATES PATENT AND TRADEMARK OFFICE
CERTIFICATE OF CORRECTION

PATENT NO. : 4,124,599
DATED : 7 November 1978
INVENTOR(S) : Robert C. Kelly

It is certified that error appears in the above—identified patent and that said Letters Patent is hereby corrected as shown below:

Column 35, lines 55-68, Formula XXIII should read as follows instead of as it appears in the patent:

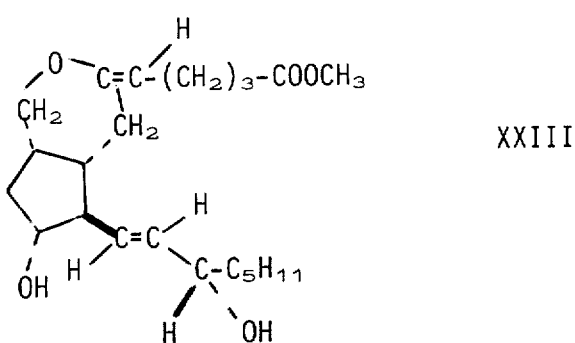

XXIII

Column 36, lines 1-14, Formula XXIV should read as follows instead of as it appears in the patent:

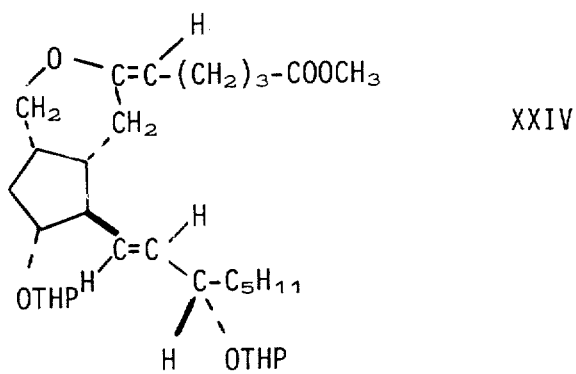

XXIV

UNITED STATES PATENT AND TRADEMARK OFFICE
CERTIFICATE OF CORRECTION

PATENT NO. : 4,124,599

DATED : 7 November 1978

INVENTOR(S) : Robert C. Kelly

It is certified that error appears in the above—identified patent and that said Letters Patent is hereby corrected as shown below:

Column 38, line 17, "-C=C-" should read -- -C≡C- --.
Column 46, line 8, "-PFG$_1$," should read -- -PGF$_1$, --.
Column 46, line 17, "-PFG$_1$," should read -- -PGF$_1$, --.
Column 46, line 21, "-PFG$_1$," should read -- -PGF$_1$, --.
Column 46, line 56, "-PFG$_1\alpha$," should read -- -PGF$_1\alpha$, --.
Column 47, line 38, "-PFG$_1$," should read -- -PGF$_1$, --.
Column 47, line 39, "-5-Iodo-5-Iodo-" should read -- -5-Iodo- --.
Column 47, line 40, "-PFG$_1$," should read -- -PGF$_1$, --.
Column 57, line 30, "trans-CH≡CH-)." should read -- trans-CH=CH-). --
Column 62, line 57, "-hyroxymethyl-" should read -- hydroxymethyl- --.
Column 62, line 58, "-Deoxy-≢ ξ,9α-" should read -- -Deoxy-6ξ,9α- --.
Column 64, line 60, "-(m-trifluoromethylphenoxy-" should read -- -(m-trifluoromethylphenoxy)- --.
Column 72, lines 10-15, the third formula should read as follows instead of as it appears in the patent:

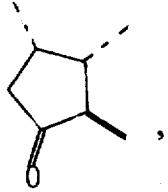

Signed and Sealed this

*Fifteenth* Day of *December 1981*

[SEAL]

Attest:

GERALD J. MOSSINGHOFF

*Attesting Officer*   *Commissioner of Patents and Trademarks*